(12) United States Patent
Freyne et al.

(10) Patent No.: US 7,947,694 B2
(45) Date of Patent: May 24, 2011

(54) SUBSTITUTED PYRAZOLO[3,4-D]PYRIMIDINES AS CELL CYCLE KINASE INHIBITORS

(75) Inventors: Eddy Jean Edgard Freyne, Rumst (BE); Jean Fernand Armand Lacrampe, Le Mesnil-Esnard (FR); Timothy Pietro Suren Perera, Geel (BE); Peter Ten Holte, Beerse (BE); Yannick Aimé Eddy Ligny, Sotteville-lès-Rouen (FR); Delphine Yvonne Raymonde Lardeau, Louviers (FR); Tom Lavrijssen, Vosselaar (BE)

(73) Assignee: Janssen Pharmaceutica NV (BE)

( * ) Notice: Subject to any disclaimer, the term of this patent is extended or adjusted under 35 U.S.C. 154(b) by 965 days.

(21) Appl. No.: 11/813,654

(22) PCT Filed: Jan. 9, 2006

(86) PCT No.: PCT/EP2006/050096
§ 371 (c)(1),
(2), (4) Date: Jul. 10, 2007

(87) PCT Pub. No.: WO2006/074984
PCT Pub. Date: Jul. 20, 2006

(65) Prior Publication Data
US 2008/0039477 A1 Feb. 14, 2008

Related U.S. Application Data

(60) Provisional application No. 60/644,766, filed on Jan. 18, 2005.

(30) Foreign Application Priority Data

Jan. 14, 2005 (EP) .................................... 05100215

(51) Int. Cl.
C07D 487/04 (2006.01)
A61K 31/519 (2006.01)
A61P 35/00 (2006.01)

(52) U.S. Cl. ..................................... 514/262.1; 544/262
(58) Field of Classification Search .................. 544/262; 514/262.1
See application file for complete search history.

(56) References Cited

U.S. PATENT DOCUMENTS 6,552,192 B1  4/2003 Hanus et al.
2004/0248905 A1  12/2004 Markwalder et al.

FOREIGN PATENT DOCUMENTS

| EP | 153976 A2 | 9/1985 |
| WO | WO 98/16184 A2 | 4/1998 |
| WO | WO 00/43394 A1 | 7/2000 |
| WO | WO 01/49688 A1 | 7/2001 |
| WO | WO 03/063764 A2 | 8/2003 |
| WO | WO 03/099820 A1 | 12/2003 |
| WO | WO 2004/065378 A1 | 8/2004 |
| WO | WO 2004/094426 A1 | 11/2004 |
| WO | WO 2006/074984 A1 | 7/2006 |

OTHER PUBLICATIONS

Mahadevan et. al. (Expert Opinion, 2007, pp. 1011-1026).*
Fischer et. al. (Expert Opin. Investig. Drugs, 2005, pp. 457-477).*
Strecker et. Al. (Expert Opin. Emerging Drugs, 2008, pp. 573-591).*
Fischer, P.M., et al., "CDK inhibitors in clinical development for the treatment of cancer", Expert Opin. Investig. Drugs, vol. 12, No. 6 (2003), pp. 955-970.
McLaughlin, F., et al., "The cell cycle, chromatin and cancer: mechanism-based therapeutics come of age", Drug Discovery Today, vol. 8, No. 17 (2003), pp. 793-802.
International Search Report PCT/EP2006/050096, mailed May 4, 2006.

* cited by examiner

Primary Examiner — Susanna Moore

(57) ABSTRACT

This invention comprises the novel compounds of formula (I)

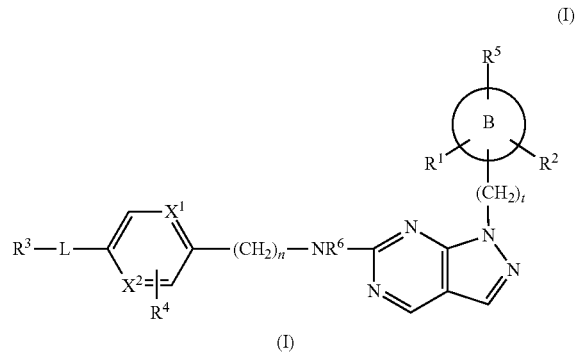

wherein $R^1$, $R^2$, $R^3$, $R^4$, $R^5$, $R^6$, $X^1$ and $X^2$ have defined meanings, having cell cycle kinase inhibiting enzymatic activity, their preparation, compositions containing them and their use as a medicine.

16 Claims, No Drawings

US 7,947,694 B2

SUBSTITUTED PYRAZOLO[3,4-D]PYRIMIDINES AS CELL CYCLE KINASE INHIBITORS

CROSS REFERENCE TO RELATED APPLICATIONS

This application is the national stage of PCT Application No. PCT/EP2006/050096, filed 9 Jan. 2006, which claims priority from European Patent Application No. 05100215.2, filed 14 Jan. 2005, and U.S. Application No. 60/644,766, filed 18 Jan. 2005, the entire disclosures of which are hereby incorporated in their entirely.

FIELD OF THE INVENTION

The present invention relates to compounds and compositions containing said compounds acting as inhibitors of cell-cycle specific kinases, more in particular the cyclin dependent kinase CDK4 and/or the Aurora kinases AURORA A and/or AURORA B. Moreover, the present invention provides processes for the preparation of the disclosed inhibitors, and methods of using them, for instance as a medicine.

In normal cells the cell cycle is a tightly regulated and carefully balanced process through which one cell divides into two. The four phases, G1, S, G2 and M phase, reflect stages in cell cycle progression where DNA synthesis and replication (S phase) and mitosis (M phase) occur in a temporally regulated fashion, separated by two gap phases (G1 and G2). Cell cycle progression is maintained by an array of regulatory decision points, governed in part by cyclin dependent kinases (Cdks), which determine whether it is appropriate for a cell to divide. In addition to the catalytic subunit (the Cdk itself), each Cdk complex contains one of many activating subunits called cyclins because their levels fluctuate periodically throughout the cell cycle. Distinct cyclin-Cdk complexes power the cell through different phases of the cell cycle. In mammals, these complexes include the D-type cyclins which activate Cdk4 to execute critical regulatory events in G1; the E-type and A-type cyclins, which activate Cdk2 to effect events in S phase including DNA replication and centrosome duplication; and A-type cyclins (in a second role) and B-type cyclins, which activate Cdk1 to direct structural and regulatory events in mitosis. Inactivation of Cdk1 in late mitosis contributes to reset the cell in G1.

An important role of Cdks is in the phosphorylation of the retinoblastoma (Rb) tumor suppression gene product whereafter E2F is released to facilitate DNA replication and progression through the cell cycle (McLaughlin et al., Drug Discovery Today. 8: 793-802 (2003)).

Cdk deregulation, either through direct or indirect mechanisms, is a typical feature in most cancer cells. Furthermore there exist a plethora of biological mechanistic indications and convincing support by preclinical studies, that Cdk inhibitors can synergise with various chemotherapeutic agents in tumor cell killing (Fisher et al. Expert Opin. Investig. Drugs. 12: 955-970 (2003)).

Also Aurora kinases play critical roles in cell division and chromosome segregation. They are implicated in the centrosome cycle, spindle assembly, chromosome condensation, microtubule-kinetochore attachment, the spindle checkpoint and cytokinesis. Aurora kinases are regulated through phosphorylation, the binding of specific partners and ubiquitin-dependent proteolysis. The deregulation of Aurora kinases impairs spindle assembly, spindle checkpoint function and cell division, causing mis-segregation of individual chromosomes or polyploidization accompanied by centrosome amplification. Aurora kinases are frequently overexpressed in cancers and the identification of Aurora A as a cancer-susceptibility gene provides a strong link between mitotic errors and carcinogenesis.

Thus pharmacological cell cycle specific kinase inhibition is an attractive strategy towards mechanism-based therapies in proliferative disorders. Moreover, the combination of cell cycle specific kinases inhibition with existing chemotherapy can have advantages effects.

BACKGROUND OF THE INVENTION

European patent application EP0961775 A2, published on 23 Apr. 1998, discloses purine L-nucleoside compounds and compositions that may be used in inflammation, infections, infestations, neoplasms, and autoimmune disease. More in particular these compounds are described as being modulators of Th1 and Th2.

European patent application EP1147108 A1, published on 27 Jul. 2000, discloses substituted nitrogen heterocyclic derivatives having immunosuppressive, antimicrobial, cytostatic, anticancer, antimitotic and antineurogenerative effects. More in particular these compounds are described as suppressors of spontaneous and mitogen activated lymphocytes and as antiviral compounds. European patent application EP1244668 A1, published on 12 Jul. 2001, discloses purine derivatives with an inhibitory effect on cyclin dependent kinases, viruses and proliferation of haematopoitic and cancer cells. More in particular the compounds are described as inhibitors of the cyclin dependent kinases that associate with type B cyclin, f.e. cdk1 and related cdks (cdk2, cdk5, cdk7 and cdk9).

European patent application EP1507780, published on 4 Dec. 2003, discloses pyrazolo-pyrimidine aniline compounds, useful as kinase inhibitors.

European application EP153976 A2, published on 4 Mar. 2004, describes 2,6,9-trisubstituted 8-azapurines as kinase inhibitors.

European patent application EP1590341 A1, published on 5 Aug. 2004, discloses pyrimidine derivatives with an inhibitory activity on cyclin-dependent kinase 4.

European patent application EP1615926 A1, published on 4 Nov. 2004, discloses purin-6-yl amino acid derivatives as anti-cancer agents.

International application WO 03/63764, published on 9 Dec. 2004, discloses 6-substituted pyrazolo[3,4-d]pyrimidin-4-ones useful as cyclin dependent kinase inhibitors The present invention relates to compounds, which are distinguishable from the prior art in structure, pharmacological activity, potency and selectivity.

DESCRIPTION OF THE INVENTION

The present invention concerns a compound of formula (I)

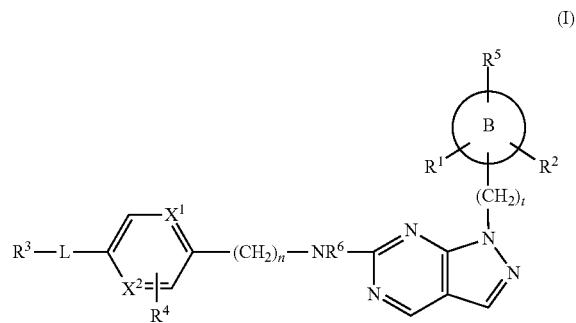

a N-oxide, an addition salt, a quaternary amine and a stereochemically isomeric form thereof, wherein $X^1$ and $X^2$ are each independently N or CH with the exception that $X^1$ and $X^2$ can not be both N;

n is an integer with value 0 or 1 and when n is 0 then a direct bond is intended;

t is an integer with value 0 or 1 and when t is 0 then a direct bond is intended;

ring B represents phenyl, cyclopentyl, cyclohexyl, norbornyl or

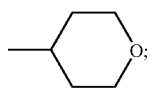

L is a direct bond, $—(CH_2)_r—NR^7—(CH_2)_s—$, $—(CR^8{}_2)_r—O—(CH_2)_s—$, $—C(=O)—$, $—(CH_2)_r—O—C(=O)—$, $—(CH_2)_r—NR^7—C(=O)—$, $—S(=O)_2—$, $—(CH_2)_r—NH—S(=O)_2—$, or $—C_{1-4}alkyl-$; wherein
each $—(CH_2)_r—$ moiety is linked to $R^3$;

each s is an integer with value 0 or 1 and when s is 0 then a direct bond is intended;

each r is an integer with value 0, 1, 2 or 3 and when r is 0 then a direct bond is intended;

each $R^7$ is hydrogen, $C_{1-6}alkyl$ or $C_{1-4}alkyloxycarbonyl$;

each $R^8$ is independently hydrogen, hydroxy or $C_{1-6}alkyl$; or two $R^8$ together can form a bivalent radical of formula $—CH_2—CH_2—$;

$R^1$, $R^2$ and $R^5$ are each independently hydrogen, hydroxy or $C_{1-6}alkyl$;

$R^3$ is hydroxy, $C_{1-6}alkyloxy$, $C_{1-6}alkyloxyC_{1-6}alkyloxy$, $—NR^9R^{10}$, $—S(=O)_2—NR^9R^{10}$; or a ring system selected from pyridinyl, triazolyl, or

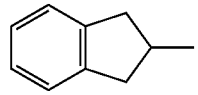

wherein each pyridinyl, triazolyl, or

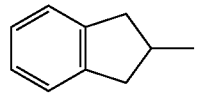

is optionally substituted with one substituent selected from hydroxy, $C_{1-6}alkyl$, hydroxy$C_{1-6}alkyl$, hydroxycyclopropyl$C_{1-6}alkyl$, hydroxy$C_{1-6}alkylcarbonyl$, hydroxycyclopropylcarbonyl, hydroxy$C_{1-6}alkyloxy$, $C_{1-6}alkyloxy$, hydroxy$C_{1-6}alkyloxyC_{1-6}alkyloxyC_{1-6}alkyl$, $C_{1-6}alkylcarbonyl$, $C_{1-4}alkyloxycarbonyl$, $C_{1-6}alkyloxyC_{1-6}alkyl$, $C_{1-6}alkyloxyC_{1-6}alkylcarbonyl$, $C_{1-6}alkyloxyC_{1-6}alkyloxy$, $C_{1-6}alkyloxyC_{1-6}alkyloxyC_{1-6}alkyl$, pyridinyl, $—NR^9R^{10}$, or $—S(=O)_2—NR^9R^{10}$;

wherein each $R^9$ and $R^{10}$ independently represent hydrogen, $C_{1-6}alkyl$, hydroxy$C_{1-6}alkyl$, hydroxycyclopropyl$C_{1-6}alkyl$, $C_{1-6}alkyloxycarbonyl$ or $C_{1-6}alkyloxyC_{1-6}alkyl$;

$R^4$ is hydrogen or halo; or $R^4$ together with -L-$R^3$— can form a bivalent radical of formula $—NH—CH=CH—$; and $R^6$ is hydrogen, $C_{1-6}alkyl$ or $C_{1-4}alkyloxycarbonyl$.

The compounds of formula (I) may also exist in their tautomeric forms. Such forms although not explicitly indicated in the above formula are intended to be included within the scope of the present invention.

A number of terms used in the foregoing definitions and hereinafter are explained hereunder. These terms are sometimes used as such or in composite terms.

As used in the foregoing definitions and hereinafter, halo is generic to fluoro, chloro, bromo and iodo; $C_{1-4}alkyl$ defines straight and branched chain saturated hydrocarbon radicals having from 1 to 4 carbon atoms such as, e.g. methyl, ethyl, propyl, butyl, 1-methylethyl, 2-methylpropyl and the like; $C_{1-6}alkyl$ includes $C_{1-4}alkyl$ and the higher homologues thereof having 5 to 6 carbon atoms such as, for example, pentyl, 2-methyl-butyl, hexyl, 2-methylpentyl and the like.

The term "addition salt" comprises the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

The term "addition salt" further comprises pharmaceutically acceptable salts, metal complexes and solvates and the salts thereof, that the compounds of formula (I) are able to form.

The term "pharmaceutically acceptable salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I) are able to form. Examples of such forms are e.g. hydrates, alcoholates and the like.

The term "metal complexes" means a complex formed between a compound of formula (I) and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g. methylsulfonates, 4-methylphenylsulfonates, salicylates, benzoates and the like of the metals of the second main group of the periodical system, e.g. the magnesium or calcium salts, of the third or fourth main group, e.g. aluminium, tin, lead as well as the first to the eighth transition groups of the periodical system such as, for example, chromium, manganese, iron, cobalt, nickel, copper, zinc and the like.

The term "stereochemically isomeric forms of compounds of formula (I)", as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

Whenever used hereinafter, the term "compounds of formula (I)" is meant to include also the N-oxide forms, the pharmaceutically acceptable acid or base addition salts and all stereoisomeric forms.

As used herein before, the term (=O) forms a carbonyl moiety when attached to a carbon atom, a sulfoxide moiety when attached to a sulfur atom and a sulfonyl moiety when two of said terms are attached to a sulfur atom.

Lines drawn into ring systems from substituents indicate that the bond may be attached to any of the suitable ring atoms of the ring system.

A first group of interesting compounds consists of those compounds of formula (I) wherein one or more of the following restrictions apply:
a) $X^1$ and $X^2$ are each CH;
b) n is 0;
c) t is 0;
d) ring B represents cyclohexyl, norbornyl or

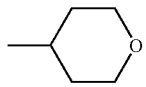

e) L is a direct bond, $-(CH_2)_r-NR^7-(CH_2)_s-$, $-(CR^8_2)_r-O-(CH_2)_s-$, $-(CH_2)_r-O-C(=O)-$, $-(CH_2)_r-NR^7-C(=O)-$ or $-(CH_2)_r-NH-S(=O)_2-$;
f) r is 0, 2 or 3;
g) each $R^7$ is hydrogen or $C_{1-4}$alkyloxycarbonyl;
h) each $R^8$ is independently hydrogen or hydroxy;
i) $R^1$, $R^2$ and $R^5$ are each independently hydrogen;
j) $R^3$ is $C_{1-6}$alkyloxy, $-NR^9R^{10}$, triazolyl, or

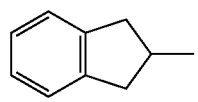

k) each $R^9$ and $R^{10}$ independently represent $C_{1-6}$alkyl;

l) $R^4$ is hydrogen or $R^4$ together with -L-$R^3$— can form a bivalent radical of formula $-NH-CH=CH-$; and
m) $R^6$ is hydrogen or $C_{1-4}$alkyloxycarbonyl.

A second group of interesting compounds consists of those compounds of formula (I) wherein one or more of the following restrictions apply:
a) $X^1$ and $X^2$ are each CH;
b) n is 0;
c) t is 0;
d) ring B represents cyclohexyl or norbornyl;
e) L is a direct bond, $-(CH_2)_r-NR^7-(CH_2)_s-$, $-(CR^8_2)_r-O-(CH_2)_s-$, $-(CH_2)_r-NR^7-C(=O)$;
f) r is 0, 2 or 3;
g) each $R^7$ is hydrogen;
h) each $R^8$ is independently hydrogen or hydroxy;
i) $R^1$, $R^2$ and $R^5$ are each independently hydrogen;
j) $R^3$ is $C_{1-6}$alkyloxy, $-NR^9R^{10}$, triazolyl, or

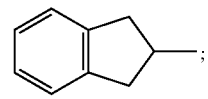

k) each $R^9$ and $R^{10}$ independently represent $C_{1-6}$alkyl;
l) $R^4$ is hydrogen; and
m) $R^6$ is hydrogen.

A third group of interesting compounds consists of those compounds of formula (I) wherein one or more of the following restrictions apply:
a) $X^1$ and $X^2$ are each CH;
b) n is 0;
c) t is 0;
d) ring B represents norbornyl;
e) L is $-(CH_2)_r-NR^7-(CH_2)_s-$;
f) s is 1;
g) r is 0 or 3;
h) each $R^7$ is hydrogen;
i) $R^1$, $R^2$ and $R^5$ are each independently hydrogen;
j) $R^3$ is $C_{1-6}$alkyloxy or

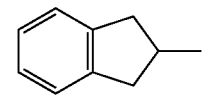

l) $R^4$ is hydrogen; and
m) $R^6$ is hydrogen.

A fourth group of interesting compounds consists of those compounds of formula (I) and those compounds of the above mentioned groups wherein ring B represents cyclohexyl or norbornyl.

A fifth group of interesting compounds consists of those compounds of formula (I) and those compounds of the above mentioned groups wherein L is $-(CH_2)_r-NR^7-CH_2-$.

A sixth group of interesting compounds consists of those compounds of formula (I) and those compounds of the above mentioned groups wherein $R^3$ is other than triazolyl, or

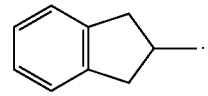

A seventh group of interesting compounds consists of those compounds of formula (I) and those compounds of the above mentioned groups wherein $R^3$, $R^6$, $R^7$, $R^9$, and $R^{10}$ are other than $C_{1-4}$alkyloxycarbonyl.

An eighth group of interesting compounds consists of those compounds of formula (I) and those compounds of the above mentioned groups wherein $X^1$ and $X^2$ are each CH.

A group of preferred compounds consists of those compounds of formula (I) wherein $X^1$ and $X^2$ are each CH; n is 0; t is 0; ring B represents cyclohexyl, norbornyl or

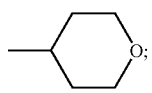

L is a direct bond, —$(CH_2)_r$—$NR^7$—$(CH_2)_s$—, —$(CR^8_2)_r$—O—$(CH_2)_s$—, —$(CH_2)_r$—O—C(=O)—, —$(CH_2)_r$—$NR^7$—C(=O)— or —$(CH_2)_r$—NH—$S(=O)_2$—; r is 0, 2 or 3; each $R^7$ is hydrogen or $C_{1-4}$alkyloxycarbonyl; each $R^8$ is independently hydrogen or hydroxy; $R^1$, $R^2$ and $R^5$ are each independently hydrogen; $R^3$ is $C_{1-6}$alkyloxy, —$NR^9R^{10}$, triazolyl, or

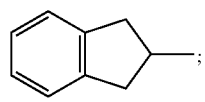

each $R^9$ and $R^{10}$ independently represent $C_{1-6}$alkyl; $R^4$ is hydrogen or $R^4$ together with -L-$R^3$— can form a bivalent radical of formula —NH—CH=CH—; and $R^6$ is hydrogen or $C_{1-4}$alkyloxycarbonyl.

A group of more preferred compounds consists of those compounds of formula (I) wherein $X^1$ and $X^2$ are each CH; n is 0; t is 0; ring B represents cyclohexyl or norbornyl; L is a direct bond, —$(CH_2)_r$—$NR^7$—$(CH_2)_s$—, —$(CR^8_2)_r$—O—$(CH_2)_s$— or —$(CH_2)_r$—$NR^7$—C(=O)—; r is 0, 2 or 3; each $R^7$ is hydrogen; each $R^8$ is independently hydrogen or hydroxy; $R^1$, $R^2$ and $R^5$ are each independently hydrogen; $R^3$ is $C_{1-6}$alkyloxy, —$NR^9R^{10}$, triazolyl, or

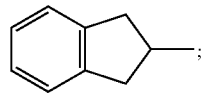

each $R^9$ and $R^{10}$ independently represent $C_{1-6}$alkyl; $R^4$ is hydrogen; and $R^6$ is hydrogen.

The most preferred compounds are compound No 1, compound No 7, compound No 2, compound No 3, compound No 6, compound No 16, compound No 4 and compound No 10.

Compound No 1

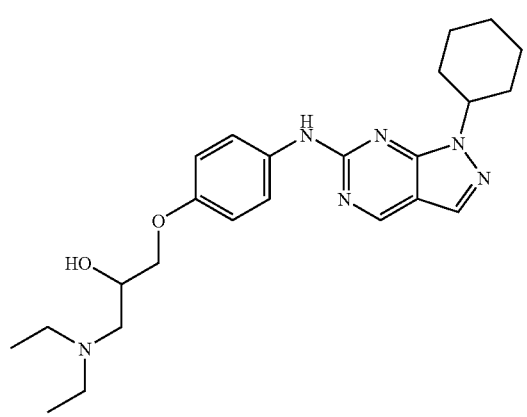

Compound No 7

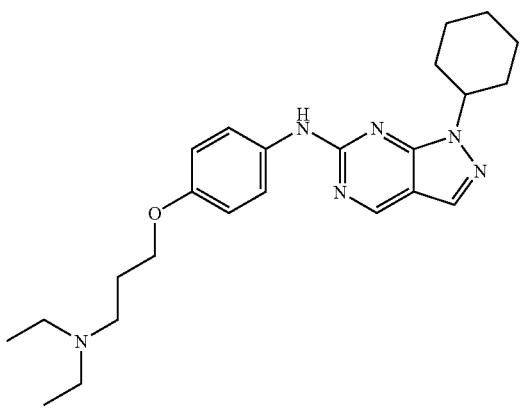

Compound No 2

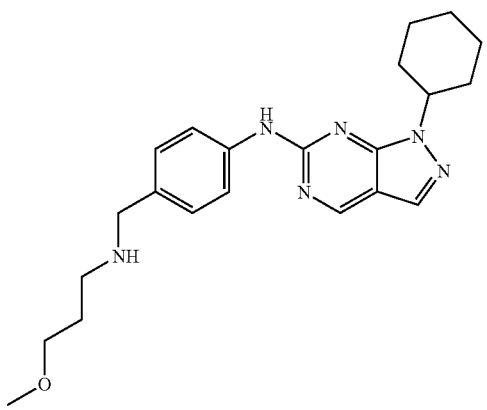

Compound No 3

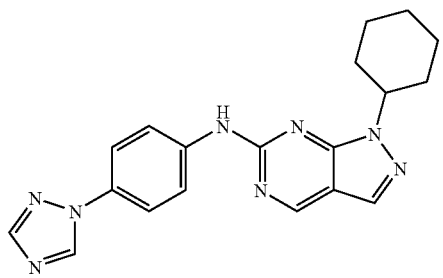

Compound No 6

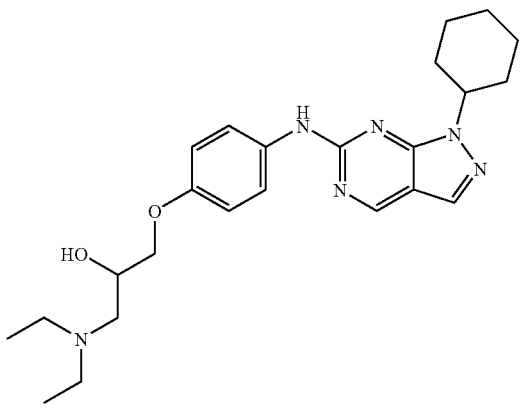

Compound No 16

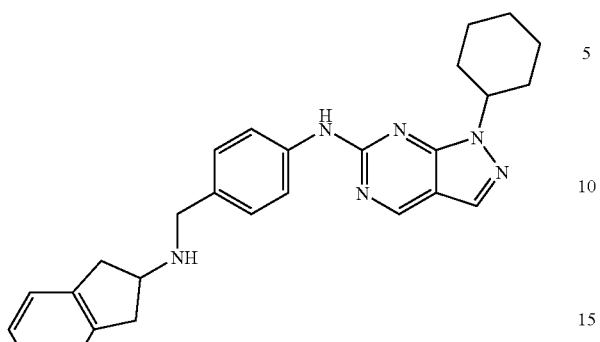

Compound No 4

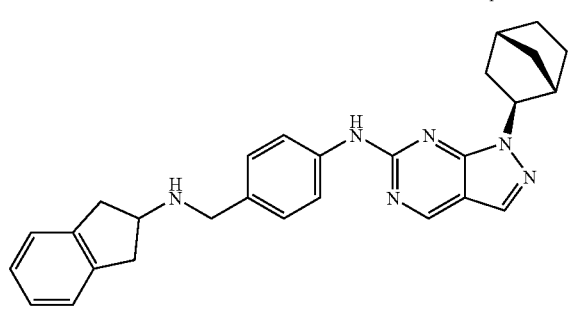

Compound No 10

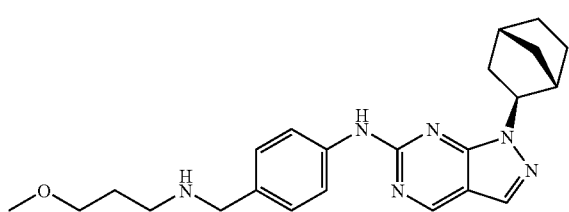

The compounds of formula (I), their pharmaceutically acceptable salts and N-oxides and stereochemically isomeric forms thereof may be prepared in conventional manner. The starting materials and some of the intermediates are known compounds and are commercially available or may be prepared according to conventional reaction procedures as generally known in the art.

A number of such preparation methods will be described hereinafter in more detail.

Compounds of formula (I) can be prepared by reacting an intermediate of formula (II) with an intermediate of formula (III) in the presence of a suitable solvent, such as for example $(CH_3)_2N$—$C(=O)H$, dimethylsulfoxide, $CH_3$—O—$CH_2$—$CH_2$—OH or an alcohol, e.g. 2-propanol and the like, optionally in the presence of a suitable base, such as for example N,N-diisopropylethanamine, NaH or 2,6-dimethylpyridine.

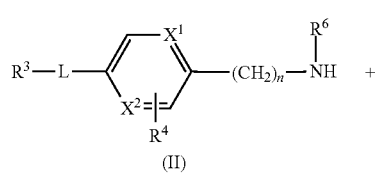

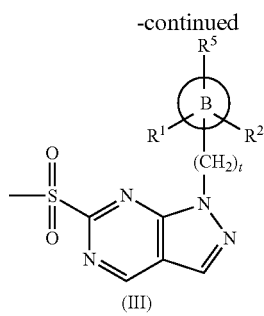

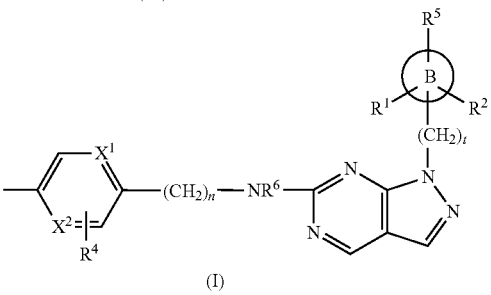

Compounds of formula (I) wherein L is —$(CH_2)_r$—NH—$C(=O)$—, herein referred to as compounds of formula (I-a), can also be prepared by reacting an intermediate of formula (XIV) with an intermediate of formula (XVI-a) in the presence of a suitable solvent, such as for example $(CH_3)_2N$—$C(=O)H$, dimethylsulfoxide, $CH_3$—O—$CH_2$—$CH_2$—OH or an alcohol, e.g. 2-propanol and the like, optionally in the presence of a suitable base, such as for example N,N-diisopropylethanamine, NaH or 2,6-dimethylpyridine.

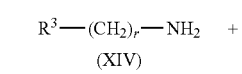

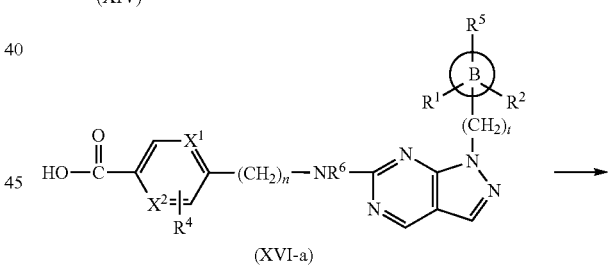

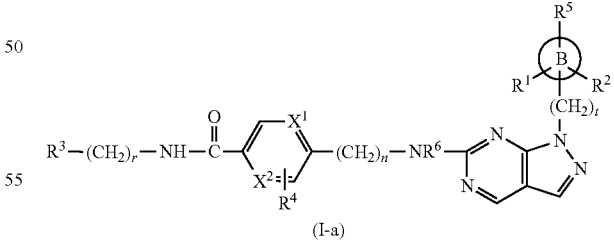

Compounds of formula (I) wherein L is —$(CH_2)_r$—$NR^7$—$CH_2$—, herein referred to as compounds of formula (I-b) can also be prepared by reacting intermediates of formula (XIV) with intermediates of formula (XVI-b) in the presence of sodium triacetoxyborohydride or sodium cyanoborohydride, in the presence of a suitable acid, such as acetic acid and in a suitable solvent, such as for example methanol or tetrahydrofuran.

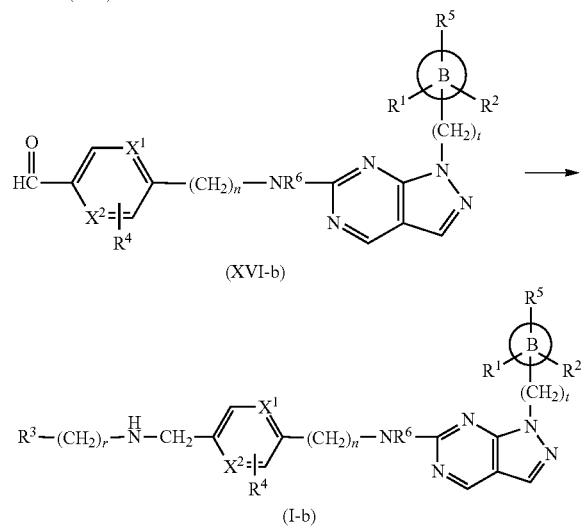

In the above reactions, the obtained compound of formula (I) can be isolated, and, if necessary, purified according to methodologies generally known in the art such as, for example, extraction, crystallization, distillation, trituration and chromatography. In case the compound of formula (I) crystallizes out, it can be isolated by filtration. Otherwise, crystallization can be caused by the addition of an appropriate solvent, such as for example water; acetonitrile; an alcohol, such as for example methanol; and combinations of said solvents. Alternatively, the reaction mixture can also be evaporated to dryness, followed by purification of the residue by chromatography (e.g. reverse phase HPLC, flash chromatography and the like). The reaction mixture can also be purified by chromatography without previously evaporating the solvent. The compound of formula (I) can also be isolated by evaporation of the solvent followed by recrystallisation in an appropriate solvent, such as for example water; acetonitrile; an alcohol, such as for example methanol; and combinations of said solvents. The person skilled in the art will recognize which method should be used, which solvent is the most appropriate to use or it belongs to routine experimentation to find the most suitable isolation method.

In this and the following preparations, the reaction products may be isolated from the reaction medium and, if necessary, further purified according to methodologies generally known in the art such as, for example, extraction, crystallization, distillation, trituration and chromatography.

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Some of the compounds of formula (I) and some of the intermediates in the present invention may consist of a mixture of stereochemically isomeric forms. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereo specifically.

An alternative manner of separating the enantiomeric forms of the compounds of formula (I) and intermediates involves liquid chromatography, in particular liquid chromatography using a chiral stationary phase.

Intermediates of formula (XVI-b) can be prepared by converting of an intermediate of formula (XVII) in the presence of a suitable acid such as trifluoroacetic acid in a suitable solvent such as $CH_2Cl_2$

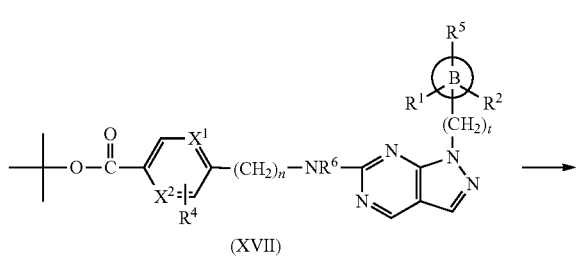

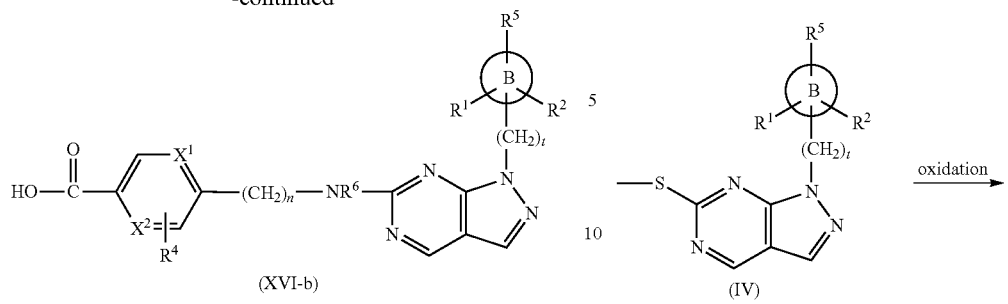

Intermediates of formula (XVII) can be prepared by reacting an intermediate of formula (XVIII) with an intermediate of formula (III) in the presence of a suitable solvent, such as for example $(CH_3)_2N$—$C(=O)H$, dimethylsulfoxide, $CH_3$—O—$CH_2$—$CH_2$—OH or an alcohol, e.g. 2-propanol and the like, optionally in the presence of a suitable base, such as for example N,N-diisopropylethanamine, Cesium carbonate, NaH or 2,6-dimethylpyridine.

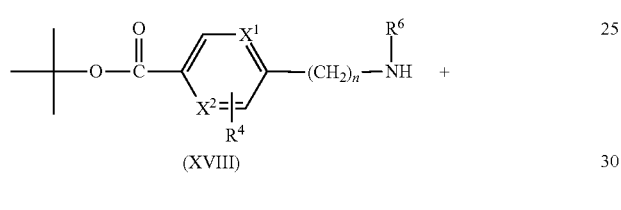

Intermediates of formula (II) can be prepared by reacting an intermediate of formula (VI) with a suitable oxidizing agent, such as for example $KMnO_4$ in the presence of a suitable solvent, such as for example water, and a suitable acid, such as for example acetic acid. An alternative suitable oxidizing agent is meta-chloroperbenzoic acid optionally in the presence of $MgSO_4$, in a suitable solvent, such as for example $CH_2Cl_2$ and optionally an alcohol, e.g. methanol and the like, optionally in the presence of morpholinomethyl PS and PS-ammonium bicarbonate scavenger.

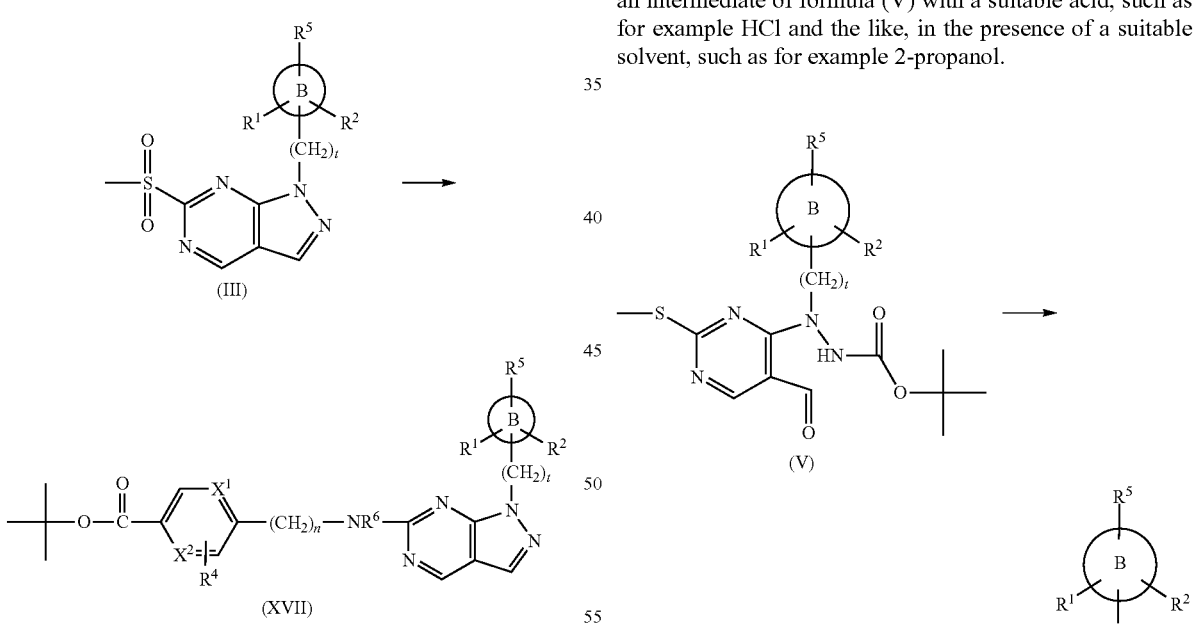

Intermediates of formula (IV) can be prepared by cyclizing an intermediate of formula (V) with a suitable acid, such as for example HCl and the like, in the presence of a suitable solvent, such as for example 2-propanol.

Intermediates of formula (V) can be prepared by reacting an intermediate of formula (VI) with a suitable agent, such as for example $MnO_2$ in the presence of a suitable solvent, such as for example $CH_2Cl_2$.

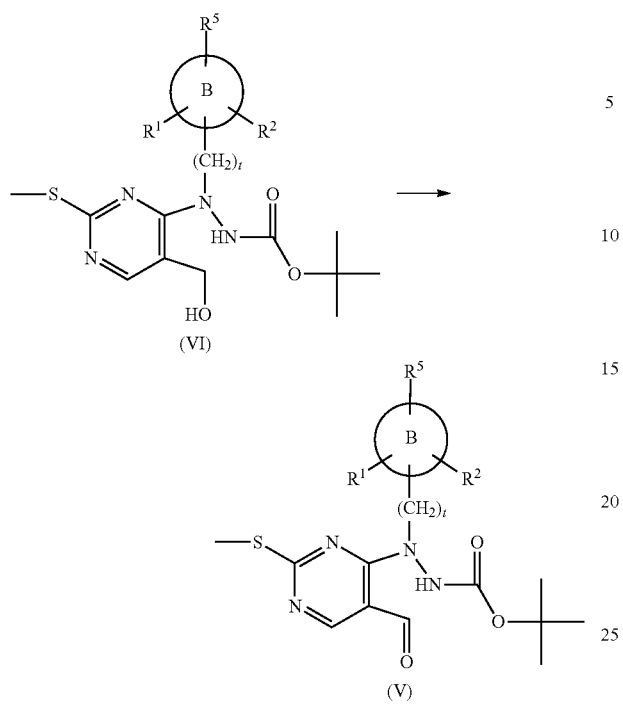

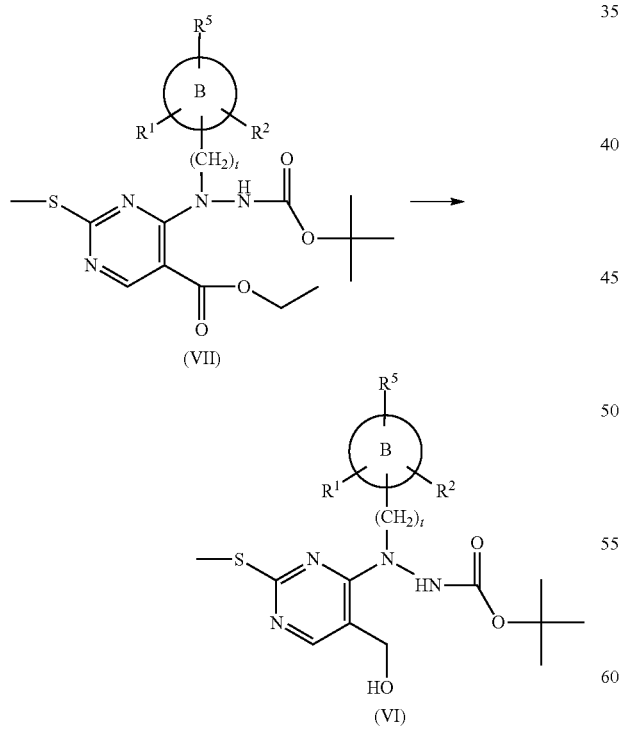

Intermediates of formula (VI) can be prepared by reacting an intermediate of formula (VII) with a suitable agent, such as for example LiAlH$_4$ in the presence of a suitable solvent, such as for example tetrahydrofuran.

Intermediates of formula (VII) can be prepared by reacting an intermediate of formula (VIII), wherein W$^2$ represents a suitable leaving group such as halogen, for example. chloro and the like, with an intermediate of formula (IX) in the presence of a suitable solvent, such as for example tetrahydrofuran, in the presence of a suitable base, such as for example N,N-diethylethanamine.

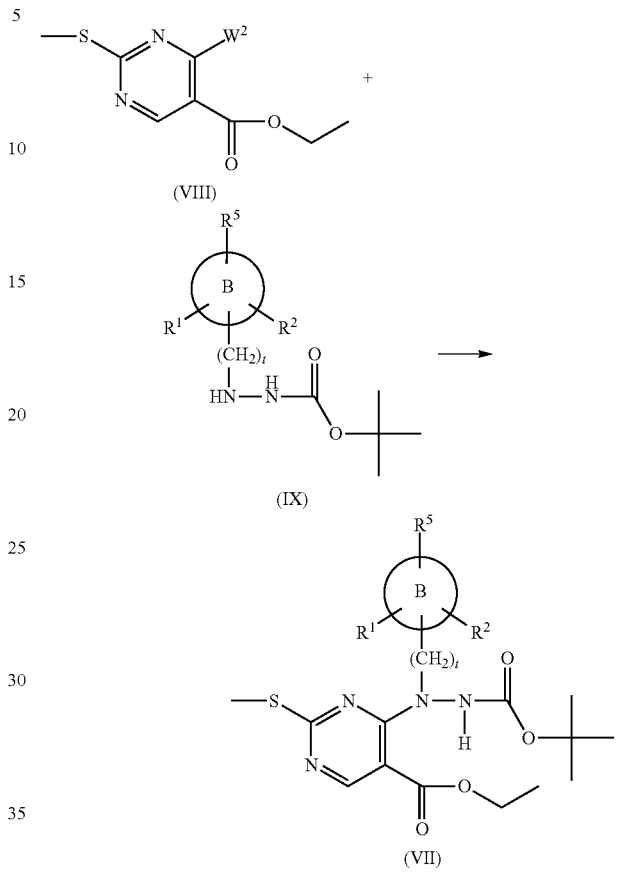

Intermediates of formula (II) wherein R$^6$ is C$_{1-4}$alkyloxycarbonyl, such as tertiary butoxycarbonyl, herein referred to as intermediates of formula (II-a), can be prepared by reacting intermediates of formula (II-a) with di-tert-butyl-dicarbonate in the presence of a suitable solvent, such as for example tetrahydrofuran, and optionally in the presence of a suitable base, such as for example N,N-diethylethanamine.

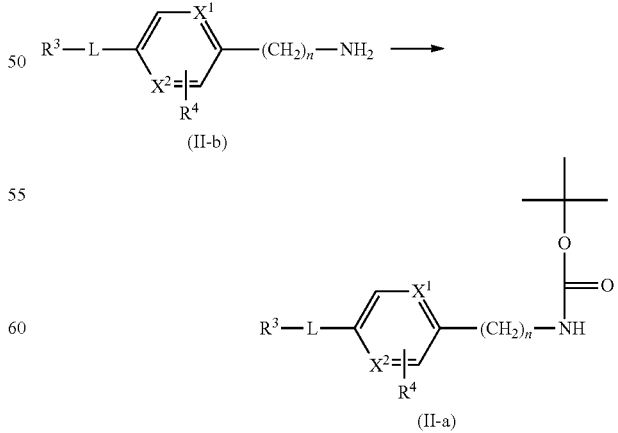

Intermediates of formula (II) wherein R$^6$ represents hydrogen, said intermediates being represented by formula (II-b), can be prepared by reacting an intermediate of formula (XI) with a suitable reducing agent, such as for example H$_2$, in the presence of a suitable catalyst, such as for example platina on charcoal or palladium on charcoal, optionally a suitable catalyst poison, such as for example a thiophene solution, a suitable solvent, such as for example N,N-dimethylacetamide, tetrahydrofuran, N,N-dimethylformamide or a suitable alcohol, such as for example methanol, and optionally in the presence of a suitable base, such as for example N,N-diethylethanamine.

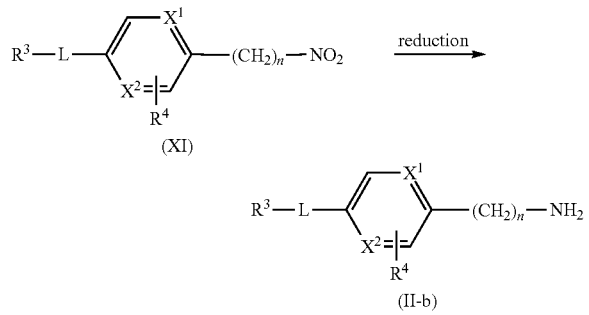

Intermediates of formula (XI) wherein L is —(CH$_2$)$_r$—NR$^7$—(CH$_2$)— and R$^7$ is C$_{1-4}$alkyloxycarbonyl, such as f.e. tertiary butoxycarbonyl, herein referred to as intermediates of formula (XI-a), can be prepared by reacting an intermediate of formula (XI) wherein L is —(CH$_2$)$_r$—NR$^7$—(CH$_2$)— and R$^7$ is hydrogen, herein referred to as intermediates of formula (XI-b), with di-tert-butyl-dicarbonate in the presence of a suitable solvent, such as for example tetrahydrofuran, and optionally in the presence of a suitable base, such as for example N,N-diethylethanamine.

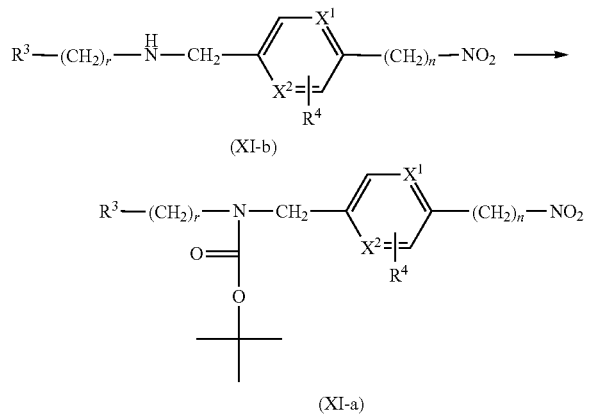

Intermediates of formula (XI-b) can be prepared by reacting intermediates of formula (XIV) with intermediates of formula (XV) in the presence of sodium triacetoxyborohydride or sodium cyanoborohydride, in the presence of a suitable acid, such as acetic acid and in a suitable solvent, such as for example methanol or tetrahydrofuran.

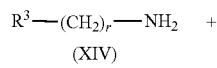

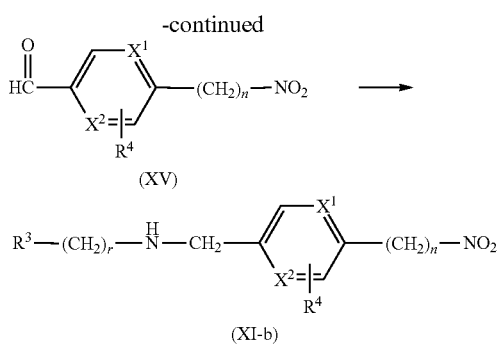

The compounds of formula (I), the pharmaceutically acceptable acid addition salts and stereoisomeric forms thereof have valuable pharmacological properties in that they are selective cell cycle specific kinase inhibitors. Specific inhibitory compounds are superior therapeutic agents since they are characterized by a greater efficacy and lower toxicity by virtue of their specificity.

The term "cell cycle specific kinase inhibitor(s)" or "inhibitor(s) of cell-cycle specific kinases" is used herein to describe an agent that inhibits at least the activity of CDK4, AURORA A and/or AURORA B in the assays described in C (pharmacological examples).

The term "CDK4" is used herein to mean a protein obtained as a result of expression of a cdk4 gene. Within the meaning of this term, CDK4 encompass all proteins encoded by a cdk4 gene, mutants thereof, and alternative slice proteins thereof. Additionally, as used herein, the term "CDK4" includes CDK4 analogues, homologues and analogues of other animals.

The term "AURORA A and/or AURORA B" is used herein to mean a protein obtained as a result of expression of an aurora gene. Within the meaning of this term, AURORA A and/or AURORA B encompass all proteins encoded by an aurora gene, mutants thereof, and alternative slice proteins thereof. Additionally, as used herein, the term "AURORA A and/or AURORA B" includes AURORA A and/or AURORA B analogues, homologues and analogues of other animals.

The term "cell cycle specific kinase", includes, but is not limited to, cyclin dependent kinases and/or aurora kinases.

The term "cyclin dependent kinases", includes but is not limited to CDK4. Within the meaning of this term CDK1, CDK2, CDK3, CDK5, CDK6, CDK7, CDK8 and CDK9 may be encompassed.

Hence, the present invention discloses the compounds of formula (I) for use as a medicine.

Furthermore, the invention also concerns the use of a compound for the manufacture of a medicament for the treatment of a disorder mediated through cell cycle specific kinases.

In particular, the invention concerns the use of a compound for the manufacture of a medicament for the treatment of a disorder mediated through CDK4, AURORA A and/or AURORA B.

Even more in particular, the invention concerns the use of a compound for the manufacture of a medicament for the treatment of a proliferative disorder or a differentiative disorder.

The term "proliferative disorder" is used herein in a broad sense to include any disorder that requires control of the cell cycle, for example cancer; cardiovascular disorders such as f.e. restenosis and cardiomyopathy; auto-immune disorders such as f.e. glomerulonephritis, rheumatoid arthritis, lupus, type I diabetis, and multiple sclerosis; dermatological disorders such as f.e. psoriasis, anti-inflammatory disorders and anti-viral disorders. In these disorders, the compounds of formula (I) may induce apoptosis or maintain stasis within the desired cells as required.

The compounds of the invention may inhibit any of the steps or stages in the cell cycle, such as for example:
formation of the nuclear envelope,
exit from the quiescent phase of the cell cycle (G0),
G1 entry,
G1 progression,
chromosome decondensation,
nuclear envelope breakdown,
START,
initiation of DNA replication,
progression of DNA replication,
termination of DNA replication,
centrosome duplication,
G2 entry,
G2 progression,
activation of mitotic or meiotic function,
chromosome condensation,
centrosome separation,
microtubule nucleation,
spindle formation and/or function,
interaction with microtubule motor proteins,
chromatid separation and segregation,
inactivation of mitotic function,
formation of the contractile ring, and/or
cytokinesis functions.

The compounds of the invention may in particular inhibit replication of RNA and DNA viruses that are dependent upon events associated with host cell proliferation and differentiation.

With the term "differentiative disorder" is meant any disorder that results from the de-differentiation of tissue which may (optionally) be accompanied by re-entry in mitosis. Such degenerative disorders include neurodegenerative diseases of the nervous system, such as f.e., Alzheimer's disease, Parkinson's disease, Huntington's disease, or amyotrophic lateral sclerosis as well as spinocerebellar degenerations. Other differentiative disorders include, for example, disorders associated with connective tissue such as may occur due to de-differentiation of chondrocytes or osteocytes, cardiovascular disorders which involve the de-differentiation of endothelial tissue and smooth muscle cells, gastric ulcers characterized by degenerative changes in glandular cells, and renal conditions marked by failure to differentiate.

The term "treating" or "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

This invention also provides a method for treating a disorder mediated through a cell cycle specific kinase by administering an effective amount of a compound of the present invention, to a subject, e.g. a mammal (and more particularly a human) in need of such treatment.

In particular, this invention provides a method for treating a disorder mediated through CDK4, AURORA A and/or AURORA B, by administering an effective amount of a compound of the present invention, to a subject, e.g. a mammal (and more particularly a human) in need of such treatment.

Even more in particular, this invention provides a method for treating a proliferative and/or a differentiative disorder, by administering an effective amount of a compound of the present invention, to a subject, e.g. a mammal (and more particularly a human) in need of such treatment.

Thus, this invention also provides a method for inhibiting tumor growth by administering an effective amount of a compound of the present invention, to a subject, e.g. a mammal (and more particularly a human) in need of such treatment.

Examples of tumors which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), oesophageal cancer, oral squamous carcinoma, tongue carcinoma, gastric carcinoma, nasopharyngeal cancer, hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, brain tumors, gliomas, benign tumor of the skin (e.g. keratoacanthomas), breast carcinoma (e.g. advanced breast cancer), kidney carcinoma, ovary carcinoma, cervical carcinoma, endometrial carcinoma, bladder carcinoma, prostate cancer including the advanced disease, testicular cancers, osteosarcoma, head and neck cancer and epidermal carcinoma.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to inhibit cell cycle specific kinases.

In particular, the compound of the invention is administered in an amount sufficient to inhibit CDK4, AURORA A and/or AURORA B or in an amount sufficient to modulate the interaction between CDK4, AURORA A and/or AURORA B and other genes and/or gene products involved in the cell cycle.

Even more in particular, the compound of the invention is administered in an amount sufficient to inhibit a proliferative disorder and/or a differentiative disorder.

With the term "other genes and/or gene products involved in the cell cycle" is meant for example genes and gene products involved in chromatin binding, formation of replication complexes, replication licensing, phosphorylation or other secondary modification activity, proteolytic degradation, microtubule binding, actin binding, septin binding, microtubule organising centre nucleation activity and binding to components of the cell cycle (signalling) pathway.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

As another aspect of the present invention, a combination of a cell cycle specific kinase inhibitor of formula (I) with another medicinal agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents. Examples of anti-cancer agents are:

platinum coordination compounds for example cisplatin, carboplatin or oxalyplatin;
taxane compounds for example paclitaxel or docetaxel;
topoisomerase I inhibitors such as camptothecin compounds for example irinotecan or topotecan;
topoisomerase II inhibitors such as anti-tumor podophyllotoxin derivatives for example etoposide or teniposide;
anti-tumor vinca alkaloids for example vinblastine, vincristine or vinorelbine;
anti-tumor nucleoside derivatives for example 5-fluorouracil, gemcitabine or capecitabine;
alkylating agents such as nitrogen mustard or nitrosourea for example cyclophosphamide, chlorambucil, carmustine or lomustine;
anti-tumor anthracycline derivatives for example daunorubicin, doxorubicin, idarubicin or mitoxantrone;
HER2 antibodies for example trastuzumab;
estrogen receptor antagonists or selective estrogen receptor modulators for example tamoxifen, toremifene, droloxifene, faslodex or raloxifene;
aromatase inhibitors such as exemestane, anastrozole, letrazole and vorozole;
differentiating agents such as retinoids, vitamin D and retinoic acid metabolism blocking agents (RAMBA) for example accutane;
DNA methyl transferase inhibitors for example azacytidine;
kinase inhibitors for example flavoperidol, imatinib mesylate or gefitinib;
farnesyltransferase inhibitors;
HDAC inhibitors;
other inhibitors of the ubiquitin-proteasome pathway for example Velcade; or
Yondelis.

The term "platinum coordination compound" is used herein to denote any tumor cell growth inhibiting platinum coordination compound which provides platinum in the form of an ion.

The term "taxane compounds" indicates a class of compounds having the taxane ring system and related to or derived from extracts from certain species of yew (*Taxus*) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree *Camptothecin acuminata* and the Indian tree *Nothapodytes foetida*.

The term "podophyllotoxin compounds" is used to indicate compounds that are related to or derived from the parent podophyllotoxin, which is extracted from the mandrake plant.

The term "anti-tumor vinca alkaloids" is used to indicate compounds that are related to or derived from extracts of the periwinkle plant (*Vinca rosea*).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumor anthracycline derivatives" comprise antibiotics obtained from the fungus Strep. peuticus var. caesius and their derivatives, characterized by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor.

Many breast cancers have estrogen receptors and growth of these tumors can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumor suppressor gene expression.

The term "kinase inhibitors" comprises potent inhibitors of kinases that are involved in cell signalling, cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone.

The term "other inhibitors of the ubiquitin-proteasome pathway" is used to identify compounds that inhibit the targeted destruction of cellular proteins in the proteasome, including cell cycle regulatory proteins.

In view of their useful pharmacological properties, the components of the combinations according to the invention, i.e. the other medicinal agent and a cell cycle specific kinase inhibitor of formula (I) may be formulated into various pharmaceutical forms for administration purposes. The components may be formulated separately in individual pharmaceutical compositions or in a unitary pharmaceutical composition containing both components.

The present invention therefore also relates to a pharmaceutical composition comprising the other medicinal agent and a cell cycle specific kinase inhibitor of formula (I) together with one or more pharmaceutical carriers.

The present invention further relates to the use of a combination according to the invention in the manufacture of a pharmaceutical composition for inhibiting a proliferative disorder and/or a differentiative disorder.

The present invention further relates to a product containing as first active ingredient a cell cycle specific kinase inhibitor of formula (I) and as second active ingredient another medicinal agent, as a combined preparation for simultaneous, separate or sequential use in the treatment of patients suffering from a proliferative disorder and/or a differentiative disorder.

The other medicinal agent and a cell cycle specific kinase inhibitor of formula (I) may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and the cell cycle specific kinase inhibitor of formula (I) being administered, their route of administration, the particular proliferative disorder and/or differentiative disorder being treated and the particular host being treated. The optimum method and order of administration and the dosage amounts and regime can be readily determined by those skilled in the art using conventional methods and in view of the information set out herein.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumor podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumor vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumor nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumor anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

Trastuzumab is advantageously administered in a dosage of 1 to 5 mg per square meter (mg/m$^2$) of body surface area, particularly 2 to 4 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

These dosages may be administered for example once, twice or more per course of treatment, which may be repeated for example every 7, 14, 21 or 28 days.

The compounds of formula (I), the acid addition salts and stereoisomeric forms thereof can have valuable diagnostic properties in that they can be used for detecting or identifying an a cell cycle specific kinase in a biological sample comprising detecting or measuring the formation of a complex between a labelled compound and/or CDK4, AURORA A and/or AURORA B and/or other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}$I, $^{131}$I, $^3$H and $^{14}$C. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase. Biological samples can be defined as body tissue or body fluids. Examples of body fluids are cerebrospinal fluid, blood, plasma, serum, urine, sputum, saliva and the like.

EXPERIMENTAL PART

Hereinafter, the term 'THF' means tetrahydrofuran, 'EtOH' means ethanol, 'LiAlH$_4$' means lithiumaluminiumhydride, 'DMSO' means dimethylsulfoxide, 'TEA' means triethylamine, 'DCM' means dichloromethane, 'EtOAc' means ethyl acetate, 'NaOAc' means sodium acetate, 'MeOH' means methanol, 'mcPBA' means 3-chlorobenzenecarboperoxoic acid, 'NaBH3CN' means sodium borocyanohydride.

A. PREPARATION OF THE INTERMEDIATE COMPOUNDS

Example A1 a) Preparation of (Intermediate 1)

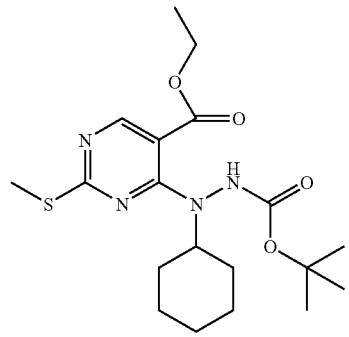

TEA (0.159 mol) was added at room temperature to a mixture of 4-chloro-2-(methylthio)-5-pyrimidinecarboxylic acid ethyl ester (0.0534 mol) and 2-cyclohexylhydrazinecarboxylic acid 1,1-dimethylethyl ester (0.1068 mol) in THF (125 ml). The mixture was stirred at room temperature overnight. The solvent was evaporated. The residue was taken up in DCM. The organic layer was washed with saturated NaHCO$_3$, dried (MgSO$_4$), filtered and the solvent was evaporated, yielding 37.2 g (>100%) of intermediate 1.

b) Preparation of (Intermediate 2)

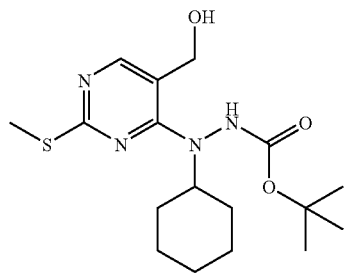

A solution of intermediate 1 ((0.0633 mol) in THF (200 ml) was added dropwise at room temperature to a suspension of LiAlH$_4$ (0.1014 mol) in THF (200 ml). The mixture was stirred at room temperature for 3 hours. EtOAc was added dropwise. Then H$_2$O (6 ml) was added. The mixture was filtered over celite. Celite was washed with EtOAc. The filtrate was evaporated. The residue (23 g) was purified by column chromatography over silica gel (35-70 μm) (eluent: DCM/MeOH/NH$_4$OH 96/4/0.5). The desired fractions were collected and the solvent was evaporated, yielding 2.2 g (9%) of intermediate 2.

c) Preparation of (Intermediate 3)

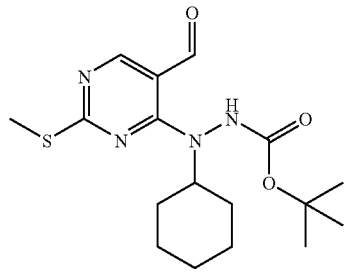

Manganese oxide (2.7 g) was added at room temperature to a mixture of intermediate 2 (0.0057 mol) in DCM (100 ml). The mixture was stirred at room temperature for 24 hours. Manganese oxide (1 g) was added. The mixture was stirred for 24 hours, then filtered over celite. The filtrate was evaporated, yielding: 2.2 g (>100%) of intermediate 3.

d) Preparation of (Intermediate 4)

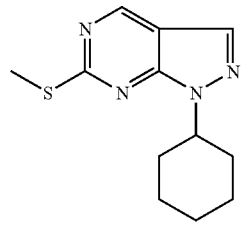

HCl/2-propanol (2.2 ml) was added at room temperature to a mixture of intermediate 3 (0.006 mol) in EtOH (20 ml). The mixture was stirred at room temperature for 5 hours. The solvent was evaporated. The residue was taken up into ice water. The aqueous layer was basified with K$_2$CO$_3$. The mixture was extracted with DCM. The organic layer was separated, dried (MgSO$_4$), filtered and the solvent was evaporated, yielding 1.3 g (88%) of intermediate 4.

e) Preparation of (Intermediate 5)

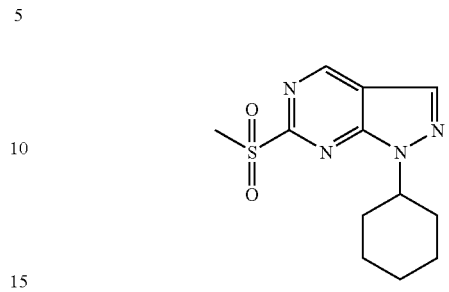

mcPBA 70% (0.0104 mol) was added at room temperature to a mixture of intermediate 4 (0.0052 mol) in DCM (30 ml). The mixture was stirred at room temperature overnight. K$_2$CO$_3$ 10% was added. The mixture was extracted with DCM. The organic layer was separated, dried (MgSO$_4$), filtered and the solvent was evaporated, yielding 1.35 g (90%) of intermediate 5.

Example A2 a) Preparation of (Intermediate 6)

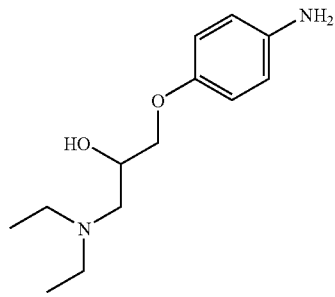

A mixture of 1-(diethylamino)-3-(4-nitrophenoxy)-2-propanol (0.026 mol) in EtOH (q.s.) was hydrogenated for 72 hours (atmospheric pressure) with Pd/C (10%) (0.7 g) as a catalyst. After uptake of H$_2$ (3 equiv), the catalyst was filtered off over celite and the filtrate was evaporated. The residue was purified by column chromatography over silica gel (eluent: DCM/(MeOH/NH$_3$ 1%) 20/1). The product fractions were collected and the solvent was evaporated, yielding 2.17 g (35%, clear oil) of intermediate 6.

Example A3 a) Preparation of (Intermediate 7)

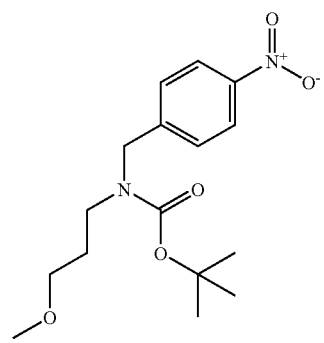

To a 100-ml 2-neck reaction flask, equipped with a magnetic stirrer, cooling and a septum, was added N-(3-methoxypropyl)-4-nitrobenzylamine (0.0098 mol). Dry THF (21 ml) and TEA (1.37 ml, 0.0098 mol) were added and the mixture was heated on an oil bath to 50° C. Then, quickly, a solution of dicarbonic acid bis(1,1-dimethylethyl)ester (0.0118 mol) in dry THF (8 ml) was added and the resultant reaction mixture was stirred for 5 hours at 50° C. The solvent was evaporated (Rotavap). The residue was purified by flash column chromatography over silica gel (eluent: hexane/EtOAc 9/1 to 1/1). The product fractions were collected and the solvent was evaporated, yielding 3.06 g (96.2%, orange oil) of intermediate 7.

b) Preparation of (Intermediate 8)

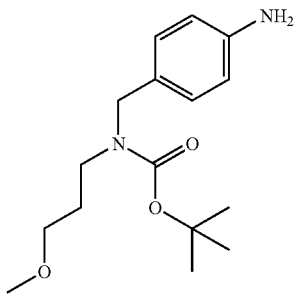

An orange solution of intermediate 7 (0.0094 mol) in MeOH (40 ml) was stirred under Argon and catalyst Pd/C (1 g) was added. The reaction solution was hydrogenated for 2 hours at room temperature with Pd/C as a catalyst. After uptake of H$_2$ (3 equiv), the catalyst was filtered off over celite and the filter residue was washed with MeOH. The filtrate's solvent was evaporated on Rotavap, yielding 2.77 g of intermediate 8.

c) Preparation of (Intermediate 9)

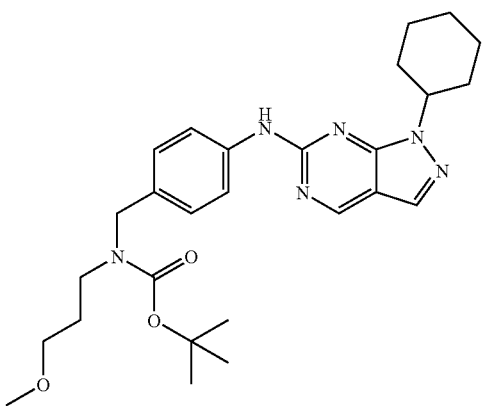

Intermediate 8 (0.001712 mol) was dried first for 10 minutes, using a vacuum pump and was then placed under Argon flow. Dry THF (1.2 ml) was added and the solution was cooled to 0° C. A 2.8 M EtMgCl/THF solution (0.31 ml, containing 0.000856 mol of EtMgCl) was added dropwise and the resultant mixture was stirred for 15 minutes at 0° C. A solution of intermediate 5 (0.000428 mol) in dry THF (1.2 ml) was added dropwise and the resultant reaction mixture was stirred for 10 minutes at 0° C., then for 2 hours at room temperature. This mixture was extracted with EtOAc/aqueous NaHCO$_3$ solution, then washed with an aqueous NaCl solution. The separated organic layer was dried (Na$_2$SO$_4$), filtered and the solvent evaporated. The residue (0.540 g) was purified by column chromatography over silica gel (eluent: DCM/diethyl ether/hexane 70/30/1). The product fractions were collected and the solvent was evaporated, yielding 0.087 g of intermediate 9.

Example A4 a) Preparation of (Intermediate 10)

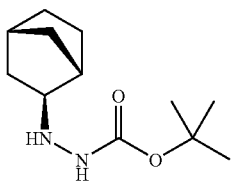

Norcamphor (50 g, 0.454 mol) and MeOH (330 ml) were added to a solution of tert butyl carbazate (60 g, 0.454 mol) in THF (330 ml). The solution was stirred at reflux for 15 hours (overnight) and then cooled to 5° C. Acetic acid (246 ml) was added. NaBH$_3$CN (57 g, 0.908 mol) was added in portions within 45 minutes, keeping the temperature below 15° C. Stirring was continued for 15 minutes at 5° C., then for 2.5 hours at room temperature. The reaction mixture was concentrated. The residue was diluted with EtOAc (500 ml) and slowly poured into a stirred 1 M aqueous Na$_2$CO$_3$ solution (gas evolution). The mixture was then stirred for 30 minutes. The organic phase was separated, the aqueous phase extracted with EtOAc. The combined EtOAc extracts were washed (saturated aqueous NaCl soln.), dried (Na$_2$SO$_4$), filtered, and concentrated to give a yellow oil (122 g). Repeated flash chromatography (DCM/EtOAc 100:0 to 80:20) afforded 20.8 g of an endo-isomer, 59 g of an impure endo-isomer, 10.7 g of an endo/exo-isomer, and 9.8 g (9.5%) g of exo-isomer intermediate 10.

b) Preparation of (Intermediate 11)

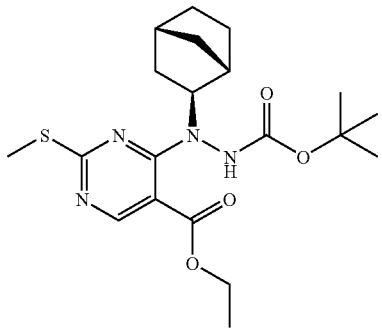

A solution of intermediate 10 (8.67 g, 38.3 mmol) in dry THF (70 ml) was added to 4-chloro-2-(methylthio)-5-pyrimidinecarboxylic acid ethyl ester (8.57 g, 36.8 mmol). The solution was cooled to 4° C. and TEA (7.7 ml, 55.2 mmol)

was slowly added. The resulting turbid solution was allowed to warm to room temperature. The mixture was stirred for 2 hours at room temperature and for 15 hours (overnight) at 65° C. The mixture was filtered, the residue was washed with EtOAc. The combined filtrate and washings were concentrated. The residue was dissolved in EtOAc and washed (H₂O, saturated aqueous NaCl solution), dried (Na₂SO₄), filtered and concentrated to give a yellow oil (16.25 g). Flash chromatography (DCM/EtOAc 95:5) afforded 14.86 g (95.5%) of intermediate 11.

c) Preparation of (Intermediate 12)

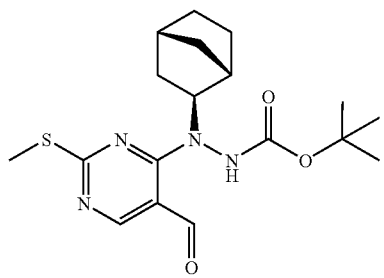

A solution of intermediate 11 (7.60 g, 18.0 mmol) in DCM (75 ml) was cooled to −76° C. A 1M solution of diisobutylaluminium hydride in hexane (90 ml, 90 mmol) was added dropwise; the temperature was kept below −65° C. The resulting yellow solution was stirred at −76° C. for 30 minutes. A 25% aqueous potassium sodium tatrate tetrahydrate solution (30 ml) was slowly added. The cooling bath was removed and the mixture was stirred for 15 minutes and poured onto a cold mixture of DCM (500 ml) and 25% aqueous potassium sodium tatrate tetrahydrate solution (500 ml). Stirring was continued for 15 minutes. The organic phase was separated, the aqueous layer was extracted with DCM (500 ml). The organic extracts were washed with half-saturated aqueous NaCl solution, combined, dried (Na₂SO₄), and concentrated to give a yellow foam. The material was dissolved in DCM (190 ml). Manganese oxide (57 g, 0.65 mol) was added in portions. The mixture was stirred for 15 minutes at room temperature and filtered through a pad of celite. The solvent was evaporated to give a yellow oil. Flash chromatography (hexane/EtOAc gradient) afforded 2.65 g (38.9%) of desired intermediate 12.

d) Preparation of (Intermediate 13)

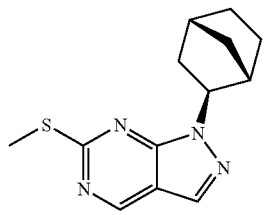

A solution of intermediate 12 (2.65 g, 7.0 mmol) in 2-propanol (27 ml) was treated with 4 M HCl in dioxane (27 ml). Gas evolution was observed. The solution was stirred at room temperature for 30 minutes, poured onto a mixture of EtOAc and a saturated aqueous NaHCO₃ solution and stirred for 15 minutes. The organic layer was separated, the aqueous layer was extracted (EtOAc). The organic phases were washed (saturated aqueous NaCl soln.), combined, dried (Na₂SO₄), filtered, and concentrated to give 1.78 g (97.8%) of intermediate 13 as yellow oil which crystallized.

e) Preparation of (Intermediate 14)

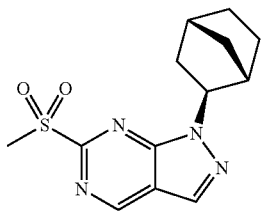

A mixture of intermediate 13 (2.10 g, 8.1 mmol) and NaOAc (1.98 g, 24.2 mmol) in DCM (68 ml) was cooled to 0° C. 3-Chloroperbenzoic acid (70%, 4.18 g, 17 mmol) was added in portions (slightly exothermic reaction). The mixture was stirred at room temperature for 1 hour. Additional 3-chloroperbenzoic acid (0.4 g, 1.6 mmol) was added and stirring continued for 30 minutes. In parallel, a second experiment starting from intermediate 13 (1.94 g, 7.5 mmol) was done. The combined mixtures were diluted with EtOAc, washed (saturated aqueous. NaHCO₃ soln., 10% aq. Na₂S₂O₃ solution, saturated aqueous NaHCO₃ solution, saturated aqueous NaCl solution), dried (Na₂SO₄), filtered, and concentrated. Flash chromatography (DCM/EtOAc 95:5) of the crude product afforded 4.04 g (88.9%) of intermediate 14 as colourless powder.

Example A5 a) Preparation of (Intermediate 15)

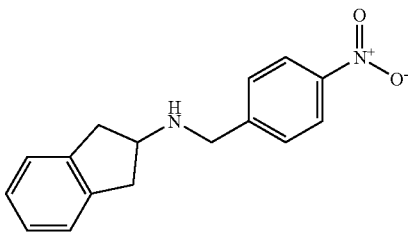

A mixture of 2-amino-indane hydrochloride (10 g, 58.9 mmol) and EtOAc was treated with 2 M aqueous Na₂CO₃ solution. The organic layer was separated and washed (2 M aqueous Na₂CO₃ solution); the aqueous layers were extracted with EtOAc. The combined organic phases were washed (saturated aqueous NaCl solution), dried (MgSO₄), filtered, and concentrated to give 2-amino-indane (7.8 g), which was dissolved in dry THF (80 ml). 4-Nitrobenzaldehyde (9.74 g, 64.4 mmol) and acetic acid (3.35 ml, 58.6 mmol) were added. The mixture was stirred at room temperature for 1 hour. NaBH(OAc)₃ (37.2 g, 176 mmol) was added. The resulting yellow suspension was stirred for 15 hours (over night). The mixture was poured onto EtOAc and 2M aqueous Na₂CO₃ solution (gas evolution). The organic phase was separated, washed (2M aqueous Na₂CO₃ solution, saturated. aqueous NaCl solution), dried (Na₂SO₄), filtered and concentrated. Flash chromatography (hexane/EtOAc 7:3) afforded 14.76 g (94%) of intermediate 15.

b) Preparation of (Intermediate 16)

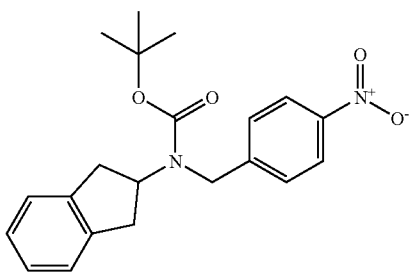

In a 500-ml three-neck round-bottom flask, intermediate 15 (0.0548 mol) was dissolved in dry THF (120 ml). TEA (7.65 ml) was added and the mixture was heated to 50° C. (oil-bath). Then, a solution of dicarbonic acid bis(1,1-dimethylethyl)ester (0.0657 mol) in dry THF (50 ml) was added quickly (gas evolution!) and the resultant reaction mixture was stirred at 50° C. The mixture was cooled to room temperature and the solvent was evaporated (Rotavap). The residue was purified by flash column chromatography over silica gel (eluent: hexane/EtOAc 95/5 to 90/10). The product fractions were collected and the solvent was evaporated, yielding 17.9 g (98.5%) of intermediate 16.

c) Preparation of (Intermediate 17)

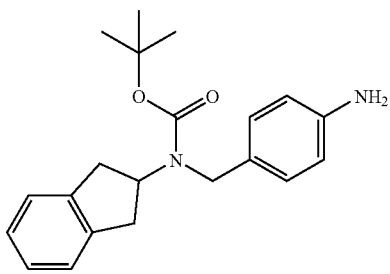

Intermediate 16 (0.0540 mol) was dissolved in MeOH (310 ml). The yellow solution was hydrogenated for 5 hours at room temperature with Pd/C (6.84 g, which was added gently under Argon flow) as a catalyst. After uptake of $H_2$ (3 equiv), the mixture was placed under Argon, then the catalyst was filtered off over celite. The filter cake was rinsed with methanol and the filtrate was evaporated (Rotavap), yielding 16.30 g (89.2%) of intermediate 17.

d) Preparation of (Intermediate 18)

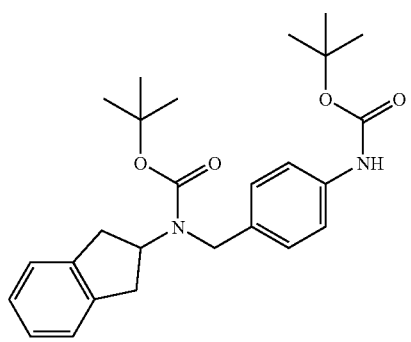

Intermediate 17 (0.01182 mol) was dissolved in dry THF (25 ml) and the solution was heated to 60° C. A solution of dicarbonic acid bis(1,1-dimethylethyl)ester (0.01478 mol) in dry THF (15 ml) was added dropwise. The reaction mixture was stirred for ±4.5 hours at 60° C. The solvent was evaporated. The residue (6.00 g) was purified by flash column chromatography over silica gel (eluent: EtOAc/hexane 5/95, 10/90, 20/80). The product fractions were collected and the solvent was evaporated, yielding 4.752 g (92%) of intermediate 18.

Example A6 a) Preparation of (Intermediate 19 and Intermediate 20)

Intermediate 19

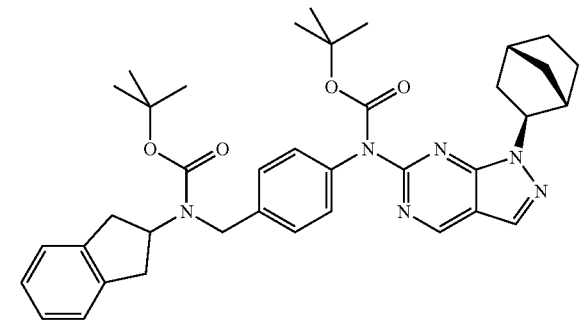

Intermediate 20

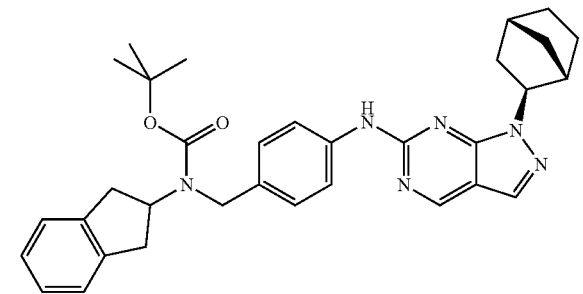

Methylmagnesium iodide (3M in diethyl ether; 200 ml, 0.6 mmol) was slowly added at 0° C. to a solution of intermediate 18 (526 mg, 1.2 mmol) in dry THF (2 ml). The mixture was stirred at 0° C. for 2 hours. A solution of intermediate 14 (70 mg, 0.24 mmol) in dry THF (2 ml) was added dropwise at 0° C. and stirring was continued for 1 hour. The mixture was poured onto saturated aqueous $NaHCO_3$ solution (30 ml) and extracted with EtOAc (50 ml). The organic phase was separated, washed ($H_2O$ (3×30 ml)), dried ($Na_2SO_4$), filtered and concentrated. The crude product (657 mg) was submitted to preparative HPLC to afford 20 mg (13%) of intermediate 19 and 90 mg (68%) of intermediate 20, both as colourless oil.

Example A7 a) Preparation of (Intermediate 21)

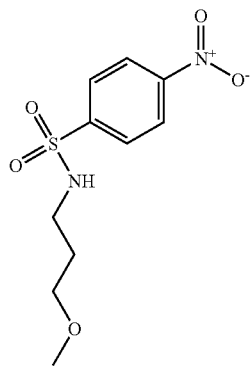

TEA (1.26 ml) was added to a solution of 3-methoxy-1-propanamine (0.009 mol) in THF (20 ml). Then 4-nitrobenzenesulfonyl chloride (0.009 mol) was added and the reaction solution was stirred for one hour at room temperature. The reaction solution was extracted with EtOAc and a saturated aqueous solution of NaHCO$_3$. The separated organic layer was dried (Na$_2$SO$_4$), filtered and the solvent evaporated, yielding 2.417 g (97.8%) of intermediate 21.

b) Preparation of (Intermediate 22)

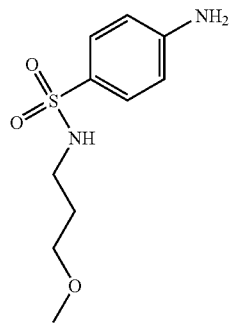

EtOH (24 ml) was added to a solution of intermediate 21 (0.00879 mol) in EtOAc (36 ml). The mixture was hydrogenated for 2 hours with Pd/C (0.360 g) as a catalyst. After uptake of H$_2$ (3 equiv), the catalyst was filtered off over celite and the filtrate was evaporated in vacuo, yielding 2.17 g of intermediate 22.

B. PREPARATION OF THE FINAL COMPOUNDS

Example B1

Preparation of (Compound 1)

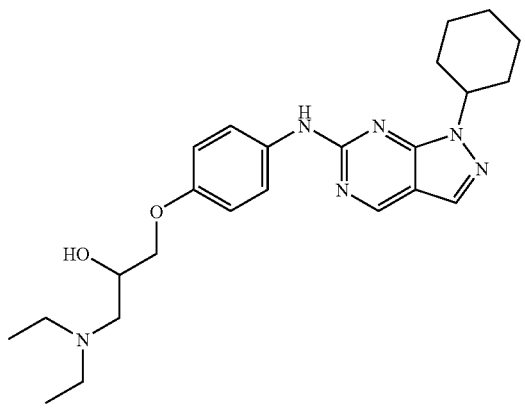

2-propanol (2 ml) was added to intermediate 5 (0.000428 mol) and intermediate 6 (0.000642 mol). Trifluoroacetic acid (0.001284 mol) was added and the resultant reaction mixture was stirred for ±20 hours at 100° C. (oil-bath). This mixture was extracted with EtOAc/NaHCO$_3$/H$_2$O/NaCl 60/30/30/30. The separated organic layer was dried (Na$_2$SO$_4$), filtered and the solvent evaporated. The residue (0.178 g) was purified by column chromatography over silica gel (eluent: DCM/(MeOH/NH$_3$) gradient). The product fractions were collected and the solvent was evaporated, yielding 0.045 g of compound 1 (oil).

Example B2

Preparation of (Compound 2)

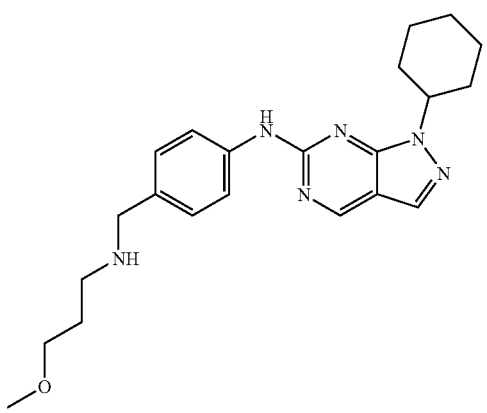

Intermediate 9 (0.000162 mol) was dissolved in a 4M HCl/dioxane solution (2.5 ml). Dissolution resulted and the yellow solution was stirred for one hour. A beige precipitation resulted. Diethyl ether was added. The mixture was filtered and the filter residue was washed with diethyl ether. The solid was dried (vacuum pump), yielding 0.056 g (87.5%) of compound 2 as a hydrochloric acid salt (1:1), melting point 212-214° C.

Example B3

Preparation of (Compound 3)

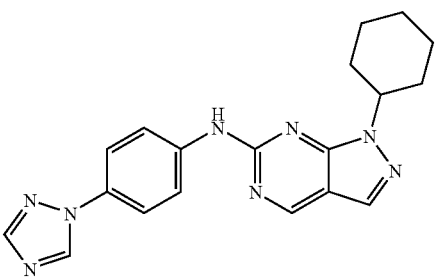

Reaction under Argon flow. Dry DMSO (0.5 ml) was added to a mixture of intermediate 5 (0.000428 mol) and 4-(1H-1, 2,4-triazol-1-yl)-benzenamine (0.000642 mol). The reaction mixture was stirred for 6 hours at 100° C. on an oil-bath (no result; only starting material). Cs₂CO₃ (0.227 g, 1.5 equiv) was added and the reaction mixture was stirred for 3 hours at 100° C. This mixture was extracted with a mixture of EtOAc/NaHCO₃/H₂O/NaCl. The extract's solvent was evaporated. The residue (0.172 g) was washed with diethyl ether, a mixture of diethyl ether/DCM, then purified by column chromatography over silica gel (eluent: toluene/2-propanone gradient). The product fractions were collected and the solvent was evaporated, yielding 0.024 g of compound 3, melting point 222.5-224° C.

Example B4

Preparation of (Compound 4)

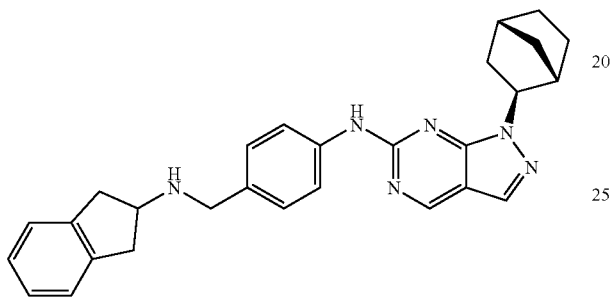

Two reactions were done separately. Reaction (I) was performed on intermediate 20 (0.000145 mol). Reaction (II) was done on intermediate 19 (0.000015 mol). To (intermediate 20 or intermediate 19) was added trifluoroacetic acid (1.5 ml) and DCM (1.5 ml). Each reaction mixture was stirred for one hour. Each mixture was extracted with EtOAc/(50 ml)/NaHCO₃ solution (30 ml)/NaCl solution (30 ml). The separated organic layer was dried (Na₂CO₃), filtered and the solvent evaporated. The aqueous phase was alkalised with NaHCO₃ to pH=9-10. The basic phase was re-extracted with EtOAc. The separated organic layer was re-extracted with a NaHCO₃ and a NaCl solution, then dried (Na₂SO₄), filtered and the solvent was evaporated, yielding 0.063 g of compound 4.

Example B5

Preparation of (Compound 5)

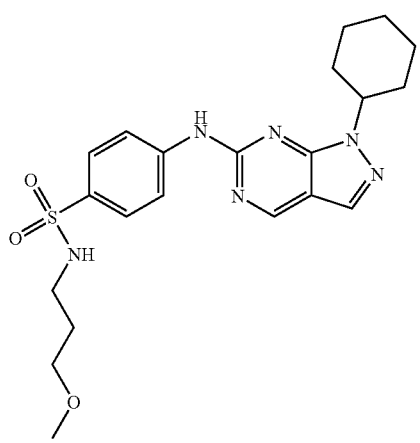

Intermediate 5 (0.000235 mol), intermediate 22 (0.000428 mol) and Cs₂CO₃ (0.000428 mol) were combined under Argon flow. DMF (0.2 ml) was added under Argon. The reaction mixture was stirred for 2 hours at 100° C. on an oil-bath. This mixture was extracted with CHCl₃/H₂O. The pH of the aqueous layer was adjusted to pH=7. This aqueous phase was re-extracted twice with CHCl₃ (no filtration). The extract's solvent was evaporated. The residue (0.174 g) was purified by column chromatography over silica gel (eluent: DCM/diethyl ether 100/0 up to 75/25). The product fractions were collected and the solvent was evaporated. The residue (0.024 g) was purified further by column chromatography over silica gel (eluent: EtOAc/hexane 1/1). The product fractions were collected and the solvent was evaporated, yielding 0.009 g of compound 5 (yellow oil).

Example B6

Preparation of (Compound 6)

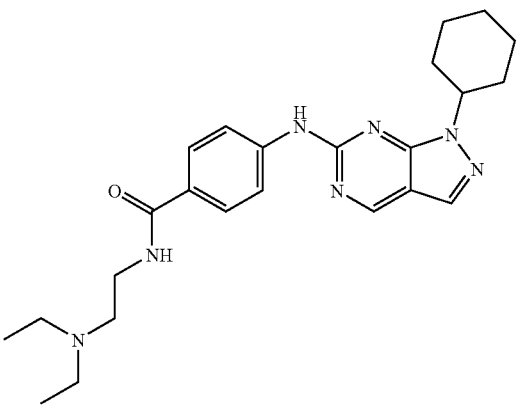

A solution of procainamide hydrochloride (2.5 g) in H₂O was treated with 2M aqueous Na₂CO₃ solution and extracted with EtOAc. The organic phase was washed (2 M aqueous Na₂CO₃ soln.), dried (Na₂SO₄), filtered and concentrated to give procainamide (2.28 g) as clear oil. A mixture of the intermediate 5 (100 mg, 0.35 mmol) and Cs₂CO₃ (174 mg, 0.53 mmol) was treated with a solution of procainamide (125 mg, 0.53 mmol) in dry DMSO (1.2 ml). The mixture was stirred at 100° C. for 5 h, followed by a normal workup (EtOAc, saturated aqueous NaHCO₃ solution, saturated aqueous NaCl soln.; Na₂SO₄). Flash chromatography (eluent: DCM/MeOH gradient then DCM/MeOH gradient containing 1% conc. aqueous NH₃ solution) and further purification by preparative TLC (eluent: DCM/MeOH containing 1% concentrated aqueous NH₃ solution) gave 20 mg (12.8%) of compound 6.

Table F-1 lists the compounds that were prepared according to the above described synthesis schemes.

TABLE F-1
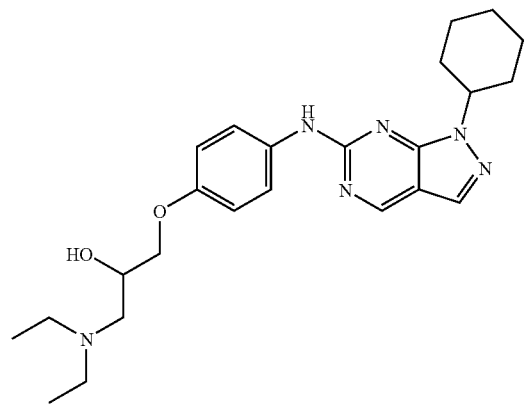
Co. No. 1; Ex. [B1]
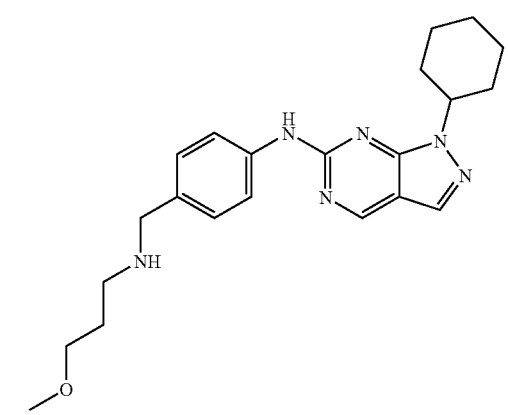
·HCl; Co. No. 2; Ex. [B2]; mp. 205-207° C.
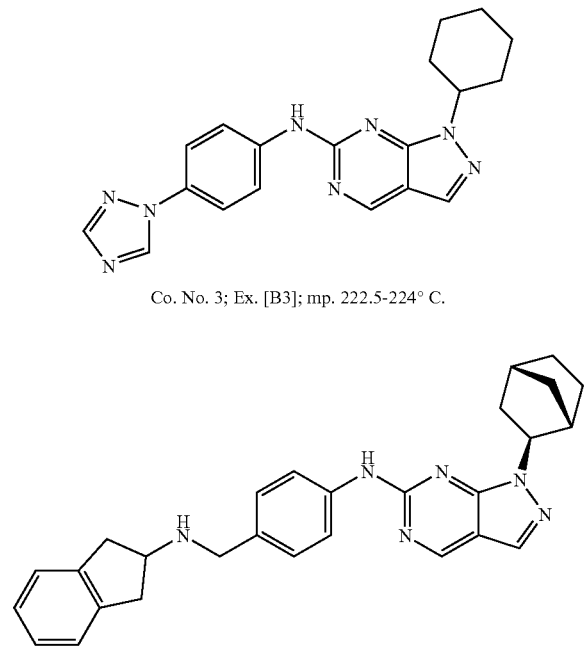
Co. No. 3; Ex. [B3]; mp. 222.5-224° C.
EXO; Co. No. 4; Ex. [B4]
TABLE F-1-continued
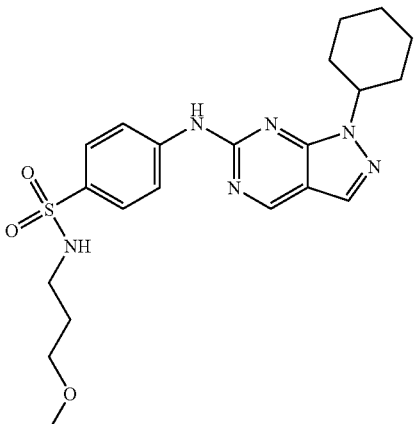
Co. No. 5; Ex. [B5]
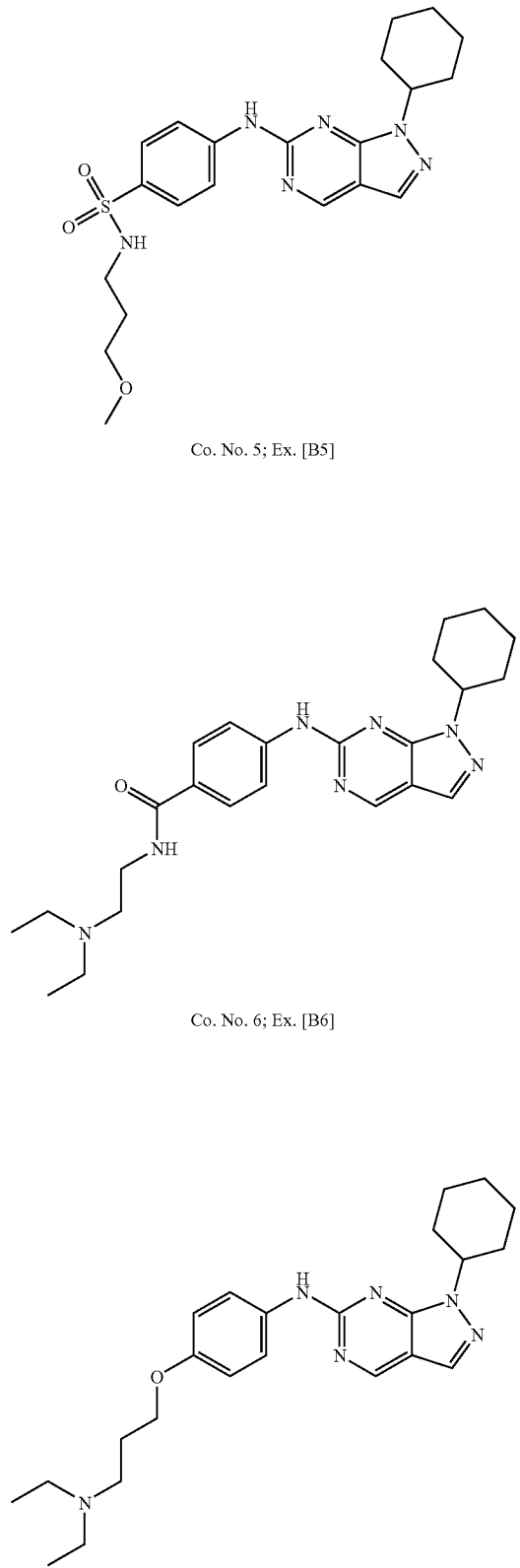
Co. No. 6; Ex. [B6]
Co. No. 7; Ex. [B1]

TABLE F-1-continued
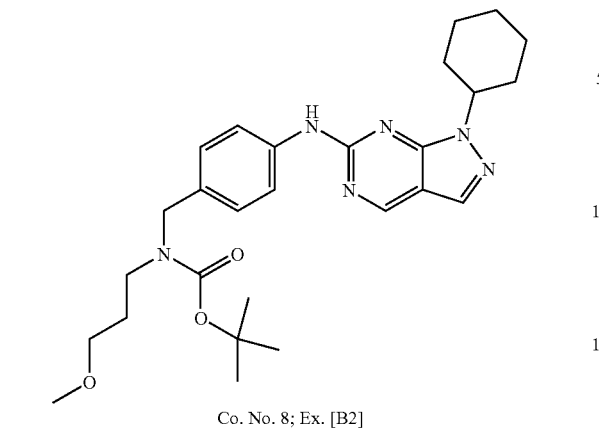
Co. No. 8; Ex. [B2]
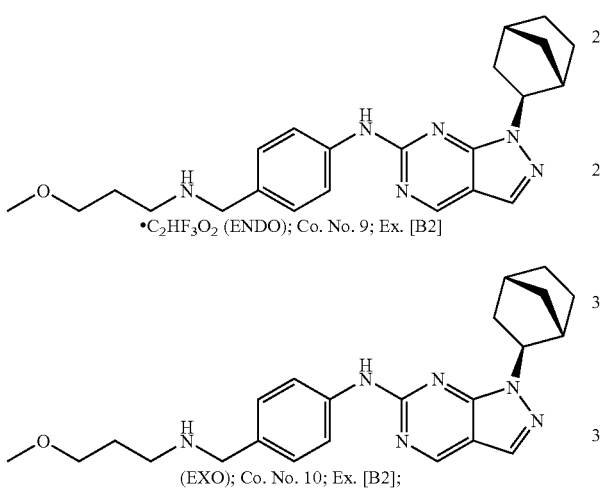
•C₂HF₃O₂ (ENDO); Co. No. 9; Ex. [B2]
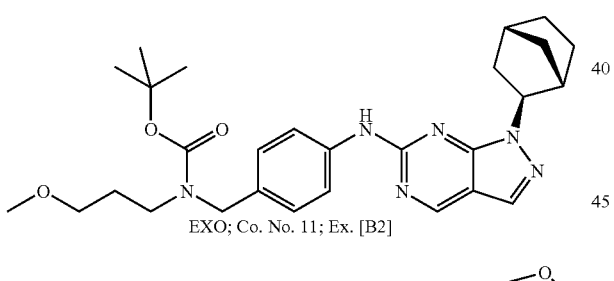
(EXO); Co. No. 10; Ex. [B2];
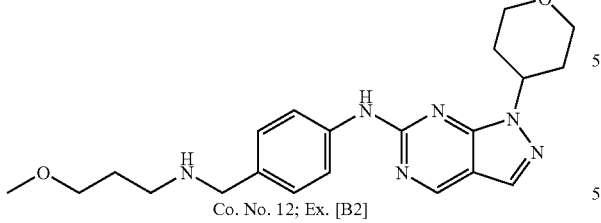
EXO; Co. No. 11; Ex. [B2]
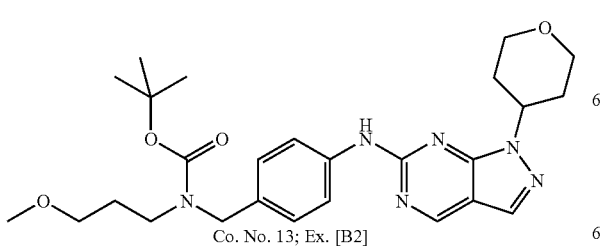
Co. No. 12; Ex. [B2]
TABLE F-1-continued
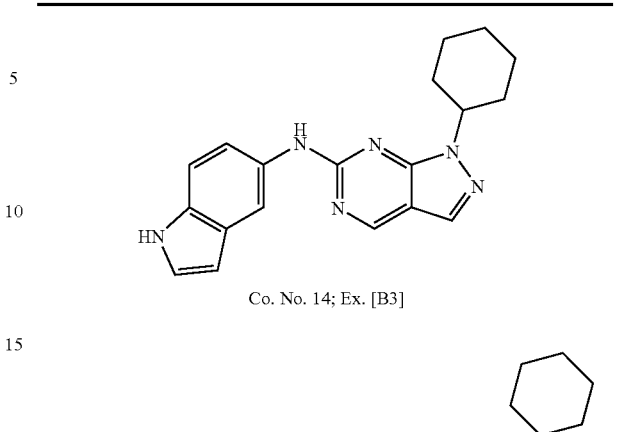
Co. No. 14; Ex. [B3]
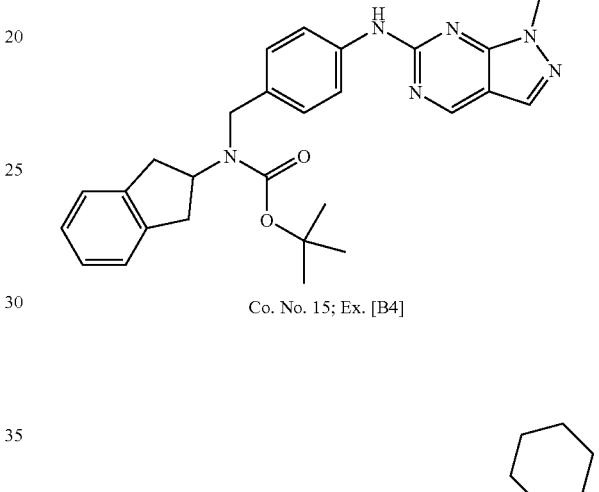
Co. No. 15; Ex. [B4]
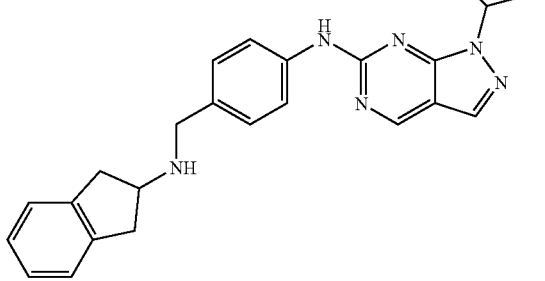
•HCl; Co. No. 16; Ex. [B4]
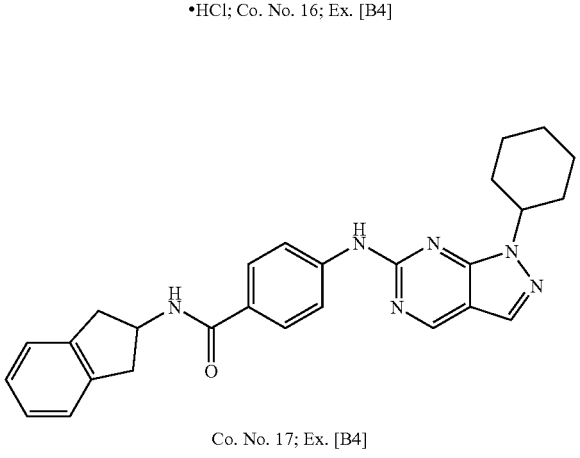
Co. No. 17; Ex. [B4]
Co. No. 13; Ex. [B2]

TABLE F-1-continued

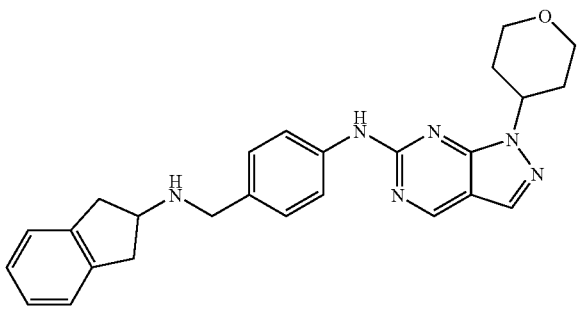

•C₂HF₃O₂; Co. No. 18; Ex. [B4]; mp. 215-220° C.

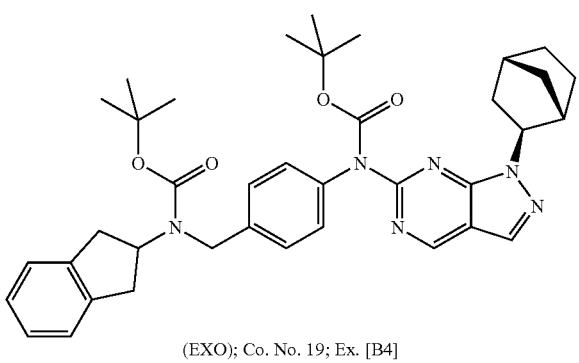

(EXO); Co. No. 19; Ex. [B4]

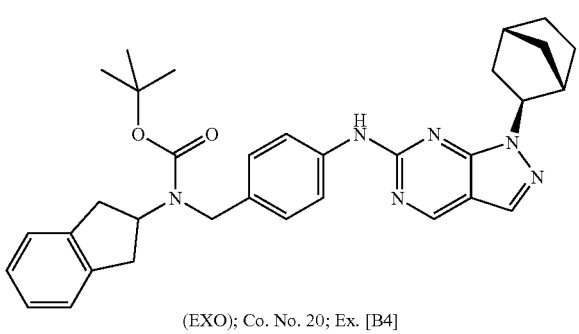

(EXO); Co. No. 20; Ex. [B4]

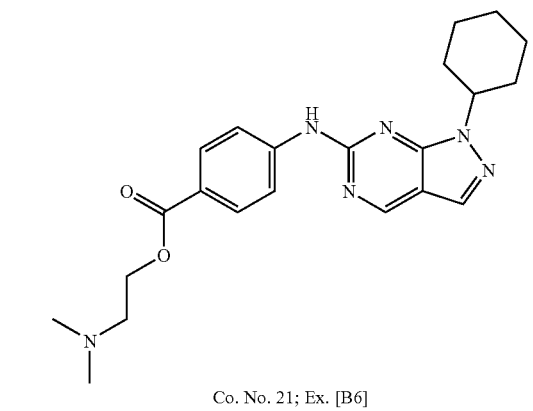

Co. No. 21; Ex. [B6]

C. PHARMACOLOGICAL EXAMPLE

The pharmacological activity of the present compounds was examined using the following test.

C.1. In Vitro Filtration Assay for CDK4 Inhibitory Activity

Compounds of the present invention were tested in an in vitro filtration assay assessing CDK4 activity by means of its pRb-phosphorylation activity using [$^{33}$P]-ATP as phosphor donor. The radioactive phosphorylated pRb is then captured on filtermats and the incorporated [$^{33}$P] quantitated using a phosphorage storage screen.

The CDK4 kinase reaction is performed at 25° C. for 45 minutes in a 96-well microtiterplate. The 25 µl reaction volume contains 50 mM Hepes pH 7.5, 10 mM NaF, 10 mM MgCl$_2$, 1 mM Na$_3$VO$_4$, 1 µM unlabeled ATP, 1 mM DTT, 0.5 µCi AT$^{33}$P, 0.76 µg/well GST-pRb, 50 ng CDK4/cyclinD1/well and 0.2% compound in 100% DMSO.

The reaction is stopped by adding 5 µl of a 3% phosphoric acid solution. 10 µl of the reaction mixture is then spotted onto a Filtermat P30 filter (Wallac) and washed 3 times for 5 min. in 75 mM phosphoric acid and 1 time for 5 min. in methanol prior to drying and quantification on the Typhoon (Amersham) using a phosphorage storage screen.

C.2. In Vitro Filtration Assay for AURORA A Inhibitory Activity

Compounds of the present invention were tested in an in vitro filtration assay assessing AURORA A activity by means of its substrate-phosphorylation activity using [$^{33}$P]-ATP as phosphor donor. The radioactive phosphorylated substrate is then captured on filtermats and the incorporated [$^{33}$P] quantitated using a phosphorage storage screen.

The Aurora-A kinase reaction is performed at 25° C. for 40 minutes in a 96-well microtiterplate. The 25 µl reaction volume contains 12 mM MOPS pH 7, 0.4 mM EDTA, 0.002% Brij35, 1% glycerol, 0.02% beta-mercapto-ethanol, 0.2 mg/ml BSA, 1 µM unlabeled ATP, 0.2 µCi [$^{33}$P]-ATP, 200 µM Kemptide, 3 ng Aurora A/well and 0.2% compound in 100% DMSO.

The reaction is stopped by adding 5 µl of a 3% phosphoric acid solution. 10 µl of the reaction mixture is then spotted onto a Filtermat P30 filter (Wallac) and washed 3 times for 5 min. in 75 mM phosphoric acid and 1 time for 5 min. in methanol prior to drying and quantification on the Typhoon (Amersham) using a phosphorage storage screen.

C.3 In Vitro Filtration Assay for AURORA B Inhibitory Activity

Compounds of the present invention were tested in an in vitro filtration assay assessing AURORA B activity by means of its substrate-phosphorylation activity using [$^{33}$P]-ATP as phosphor donor. The radioactive phosphorylated substrate is then captured on filtermats and the incorporated [$^{33}$P] quantitated using a phosphorage storage screen.

The Aurora-B kinase reaction is performed at 25° C. for 40 minutes in a 96-well microtiterplate. The 25 µl reaction volume contains 60 mM Hepes pH 7.5, 3 mM MgCl$_2$, 3 mM MnCl$_2$, 3 µM Na$_3$VO$_4$, 50 µg/ml PEG20000, 1 µM unlabeled ATP, 1 mM DTT, 0.2 µCi AT$^{33}$P, 0.25 µg/well peptide (C(LR-RWSLG)×4), 100 ng Aurora-B/well and 0.2% compound in 100% DMSO.

The reaction is stopped by adding 5 µl of a 3% phosphoric acid solution. 10 µl of the reaction mixture is then spotted onto a Filtermat P30 filter (Wallac) and washed 3 times for 5 min. in 75 mM phosphoric acid and 1 time for 5 min. in methanol prior to drying and quantification on the Typhoon (Amersham) using a phosphorage storage screen.

C.4. Calculation of pIC$_{50}$ Values

For each experiment, controls (containing enzyme (complex) and DMSO without compound), a blank incubation (containing DMSO but no enzyme (complex) or compound) and samples (containing enzyme (complex) and compound dissolved in DMSO) were run in parallel. All compounds tested were dissolved and eventually further diluted in DMSO. In first instance, compounds were tested at a concentration of $10^{-5}$ M. When the compounds showed activity at $10^{-5}$ M, a dose-response curve was made wherein the compounds were tested at concentrations between $10^{-5}$M and $10^{-8}$M. In each test, the blank value was subtracted from both the control and the sample values. The control sample represented maximal enzyme activity. For each sample, the amount of cpm was expressed as a percentage of the mean cpm value of the controls. When appropriate, $IC_{50}$-values (concentration of the drug, needed to reduce the enzyme activity to 50% of the control) were computed using linear interpolation between the experimental points just above and below the 50% level. Herein the effects of test compounds are expressed as $pIC_{50}$ (the negative log value of the $IC_{50}$-value). The inhibitory activity of the tested compounds of the invention is shown in Table-2

TABLE F-2

Table F-2 lists the results of the compounds that were tested according to example C.1, C.2 and C.3

| Co. No. | cdk4 filter see C.1 | Aurora A see C.2 | Aurora B see C.3 |
|---|---|---|---|
| 1 | 8.1 | 5.8 | <5.0 |
| 2 | 8.2 | 6.8 | <5.0 |
| 3 | 7.8 | 6.9 | 5.1 |
| 4 | 7.6 | 6.5 | 6.5 |
| 5 | 5.9 | 6.2 | <5.0 |
| 6 | 7.6 | 5.8 | <5.0 |
| 7 | 7.7 | <5.0 | <5.0 |
| 8 | 6.0 | 6.2 | <5.0 |
| 9 | 7.1 | 6.6 | 6.8 |
| 10 | 7.5 | 6.7 | 6.7 |
| 11 | 5.7 | 6.1 | 5.3 |
| 12 | 6.2 | 5.4 | 5.1 |
| 13 | 5.7 | 7.0 | 6.1 |
| 14 | 6.8 | 6.5 | 5.1 |
| 15 | <5.0 | 6.0 | <5.0 |
| 16 | 7.9 | 6.6 | 5.1 |
| 17 | 7.2 | 6.5 | 6.3 |
| 18 | 7.2 | 5.5 | 5.2 |
| 19 | <5.0 | 6.8 | 6.2 |
| 20 | <5.0 | 5.2 | <5.0 |
| 21 | 7.0 | 6.2 | 5.1 |

The compounds were further evaluated on in vitro assays measuring inhibition of different kinase activities, on cell lines and eventually in in vivo tests.

C.5. Analytical Data

The mass of the compounds was recorded with LCMS (liquid chromatography mass spectrometry). The analytical HPLC (column: Develosil RPAq 4.6×50 mm) was performed with different gradient eluent systems at a flow rate of 1.5 ml/min with UV detection at 220 nm and 254 nm. Different eluent systems were used which are described below. The data are gathered in Table F-3 below.

System A: 5% acetonitrile, 95% water (0.1% trifluoro acetic acid) to 100% acetonitrile in 5 min
System B: 10% acetonitrile, 90% water (0.1% trifluoro acetic acid) to 100% acetonitrile in 5 min
System C: 20% acetonitrile, 80% water (0.1% trifluoro acetic acid) to 100% acetonitrile in 5 min
System D: 30% acetonitrile, 70% water (0.1% trifluoro acetic acid) to 100% acetonitrile in 5 min
System E: 40% acetonitrile, 60% water (0.1% trifluoro acetic acid) to 100% acetonitrile in 5 min
System F: 50% acetonitrile, 50% water (0.1% trifluoro acetic acid) to 100% acetonitrile in 5 min
System G: 10% acetonitrile, 90% water (0.1% trifluoro acetic acid) to 30% acetonitrile, 70% water (0.1% trifluoro acetic acid) in 5 min
System H: 10% acetonitrile, 90% water (0.1% trifluoro acetic acid) to 40% acetonitrile, 60% water (0.1% trifluoro acetic acid) in 5 min
System I: 60% acetonitrile, 40% water (0.1% trifluoro acetic acid) to 100% acetonitrile in 5 min
System J: 80% acetonitrile, 20% water (0.1% trifluoro acetic acid) to 100% acetonitrile in 5 min
System K: 15% acetonitrile, 85% water (0.1% trifluoro acetic acid) to 100% acetonitrile in 5 min
System L: 70% acetonitrile, 30% water (0.1% trifluoro acetic acid) to 100% acetonitrile in 5 min

TABLE F-3

LCMS parent peak and retention time values.

| Co. No. | Retention time (minutes) | LCMS [M + H] | Eluent System |
|---|---|---|---|
| 1 | 3.76 | 439 | A |
| 2 | 3.57 | 471 | B |
| 3 | 4.28 | 361 | K |
| 4 | 4.41 | 451 | A |
| 5 | 3.84 | 445 | D |
| 6 | 3.86 | 436 | A |
| 7 | 3.94 | 423 | A |
| 8 | 1.97 | 495 | L |
| 9 | 3.70 | 407 | A |
| 10 | 4.00 | 407 | A |
| 12 | 3.29 | 397 | A |
| 13 | 2.71 | 497 | E |
| 14 | 3.96 | 333 | C |
| 16 | 4.11 | 439 | B |
| 17 | 2.24 | 453 | I |
| 18 | 3.73 | 441 | A |
| 19 | 3.09 | 651 | J |
| 20 | 2.79 | 507 | I |
| 21 | 3.77 | 409 | B |

The invention claimed is:

1. A compound of formula (I), (I)

[Chemical structure showing formula (I) with ring B bearing substituents $R^1$, $R^2$, $R^5$, connected via $(CH_2)_t$ to a pyrazolopyridine system linked through $NR^6$—$(CH_2)_n$— to a ring containing $X^1$, $X^2$, $R^4$, connected to $R^3$—L—]

a N-oxide, an addition salt, a quaternary amine and a stereochemically isomeric form thereof, wherein $X^1$ and $X^2$ are each independently N or CH with the exception that $X_1$ and $X_2$ can not be both N;

n is an integer with value 0 or 1 and when n is 0 then a direct bond is intended;

t is an integer with value 0 or 1 and when t is 0 then a direct bond is intended;

ring B represents phenyl, cyclopentyl, cyclohexyl, norbornyl or

[tetrahydropyran structure];

L is a direct bond, —(CH$_2$)$_r$—NR$^7$—(CH$_2$)$_s$—, —(CR$^8_2$)$_r$—O—(CH$_2$)$_s$—, —C(=O)—, —(CH$_2$)$_r$—O—C(=O)—, —(CH$_2$)$_r$—NR$^7$—C(=O)—, —S(=O)$_2$—, —(CH$_2$)$_r$—NH—S(=O)$_2$—, or —C$_{1-4}$alkyl-; wherein each —(CH$_2$)$_r$— moiety is linked to R$^3$;

each s is an integer with value 0 or 1 and when s is 0 then a direct bond is intended;

each r is an integer with value 0, 1, 2 or 3 and when r is 0 then a direct bond is intended;

each R$^7$ is hydrogen, C$_{1-6}$alkyl or C$_{1-4}$alkyloxycarbonyl;

each R$^8$ is independently hydrogen, hydroxy or C$_{1-6}$alkyl; or two R$^8$ together can form a bivalent radical of formula —CH$_2$—CH$_2$—;

R$^1$, R$^2$ and R$^5$ are each independently hydrogen, hydroxy or C$_{1-6}$alkyl;

R$^3$ is hydroxy, C$_{1-6}$alkyloxy, C$_{1-6}$alkyloxyC$_{1-6}$alkyloxy, —NR$^9$R$^{10}$, —S(=O)$_2$—NR$^9$R$^{10}$; or a ring system selected from pyridinyl, triazolyl, or

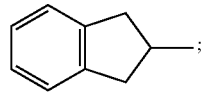

wherein each pyridinyl, triazolyl, or

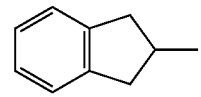

is optionally substituted with one substituent selected from hydroxy, C$_{1-6}$alkyl, hydroxyC$_{1-6}$alkyl, hydroxycyclopropylC$_{1-6}$alkyl, hydroxyC$_{1-6}$alkylcarbonyl, hydroxycyclopropylcarbonyl, hydroxyC$_{1-6}$alkyloxy, C$_{1-6}$alkyloxy, hydroxyC$_{1-6}$alkyloxyC$_{1-6}$alkyloxyC$_{1-6}$alkyl, C$_{1-6}$alkylcarbonyl, C$_{1-4}$alkyloxycarbonyl, C$_{1-6}$alkyloxyC$_{1-6}$alkyl, C$_{1-6}$alkyloxyC$_{1-6}$alkylcarbonyl, C$_{1-6}$alkyloxyC$_{1-6}$alkyloxy, C$_{1-6}$alkyloxyC$_{1-6}$alkyloxyC$_{1-6}$alkyl, pyridinyl, —NR$^9$R$^{10}$, or —S(=O)$_2$—NR$^9$R$^{10}$;

wherein each R$^9$ and R$^{10}$ independently represent hydrogen, C$_{1-6}$alkyl, hydroxyC$_{1-6}$alkyl, hydroxycyclopropylC$_{1-6}$alkyl, C$_{1-6}$alkyloxycarbonyl or C$_{1-6}$alkyloxyC$_{1-6}$alkyl;

R$^4$ is hydrogen or halo; or

R$^4$ together with -L-R$^3$— can form a bivalent radical of formula —NH—CH=CH—; and R$^6$ is hydrogen, C$_{1-6}$alkyl or C$_{1-4}$-alkyloxycarbonyl.

2. A compound as claimed in claim 1 wherein X$^1$ and X$^2$ are each CH.

3. A compound as claimed in claim 1 wherein X$^1$ and X$^2$ are each CH; n is 0; t is 0; ring B represents cyclohexyl, norbornyl or

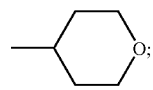

L is a direct bond, —(CH$_2$)$_r$—NR$^7$—(CH$_2$)$_s$—, —(CR$^8_2$)$_r$—O—(CH$_2$)$_s$—, —(CH$_2$)$_r$—O—C(=O)—, —(CH$_2$)$_r$—NR$^7$—C(=O)— or —(CH$_2$)$_r$—NH—S(=O)$_2$—; r is 0, 2 or 3; each R$^7$ is hydrogen or C$_{1-4}$-alkyloxycarbonyl; each R$^8$ is independently hydrogen or hydroxy; R$^1$, R$^2$ and R$^5$ are each independently hydrogen; R$^3$ is C$_{1-6}$alkyloxy, —NR$^9$R$^{10}$, triazolyl, or

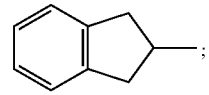

each R$^9$ and R$^{10}$ independently represent C$_{1-6}$alkyl; R$^4$ is hydrogen or R$^4$ together with -L-R$^3$— can form a bivalent radical of formula —NH—CH=CH—; and R$^6$ is hydrogen or C$_{1-4}$alkyloxycarbonyl.

4. A compound as claimed in claim 1 wherein X$^1$ and X$^2$ are each CH; n is 0; t is 0; ring B represents cyclohexyl or norbornyl; L is a direct bond, —(CH$_2$)$_r$—NR$^7$—(CH$_2$)$_s$—, —(CR$^8_2$)$_r$—O—(CH$_2$)$_a$— or —(CH$_2$)$_r$—NR$^7$—C(=O);

r is 0, 2 or 3; each R$^8$ is hydrogen; each R$^8$ is independently hydrogen or hydroxy;

R$^1$, R$^2$ and R$^5$ are each independently hydrogen; R$^3$ is C$_{1-6}$alkyloxy, —NR$^9$R$^{10}$, triazolyl, or

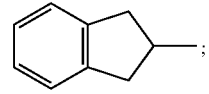

each R$^9$ and R$^{10}$ independently represent C$_{1-6}$alkyl; R$^4$ is hydrogen; and R$^6$ is hydrogen.

5. A compound selected from the group consisting of:

Compound No 1

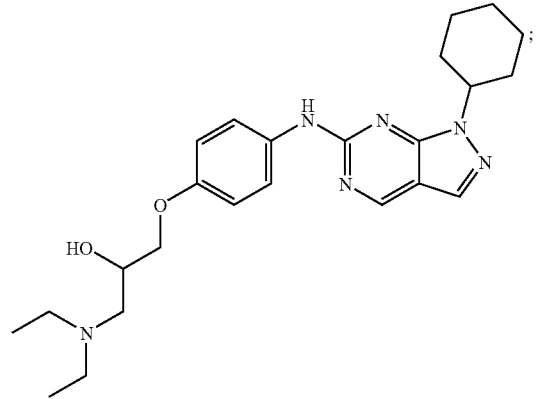

Compound No 7

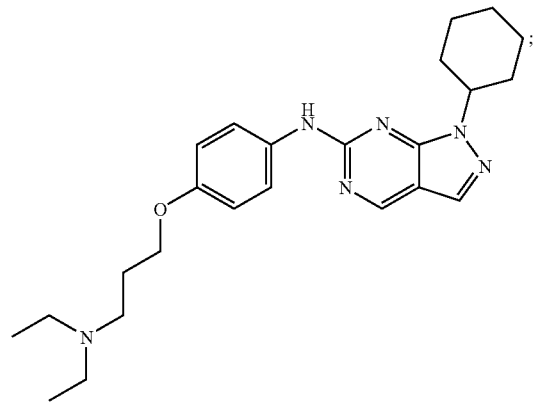

Compound No 2

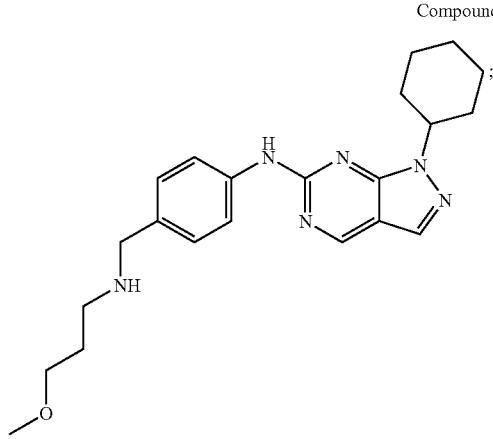

Compound No 3

Compound No 6

Compound No 16

Compound No 4

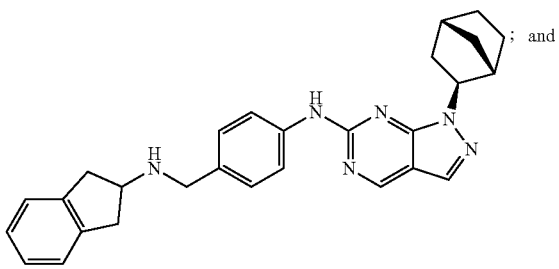

; and

Compound No 10

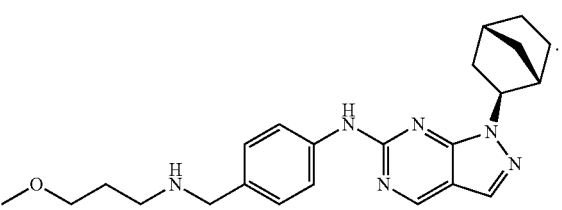

6. A pharmaceutical composition comprising pharmaceutically acceptable carriers and as an active ingredient a therapeutically effective amount of a compound as claimed in claim 1.

7. A process of preparing a pharmaceutical composition wherein the pharmaceutically acceptable carriers and a compound as claimed in claim 1 are mixed.

8. A combination of an anti-cancer agent and a cell cycle kinase inhibitor as claimed in claim 1.

9. A process for preparing a compound as claimed in claim 1, said process comprising a) reacting an intermediate of formula (II) with an intermediate of formula (III) in the presence of a suitable solvent and optionally in the presence of a suitable base, resulting in a compound of formula (I),

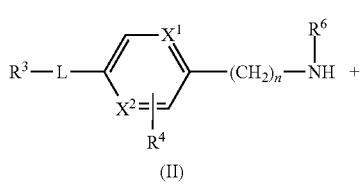

(II)

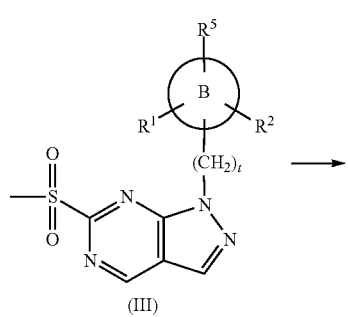

(III)

-continued

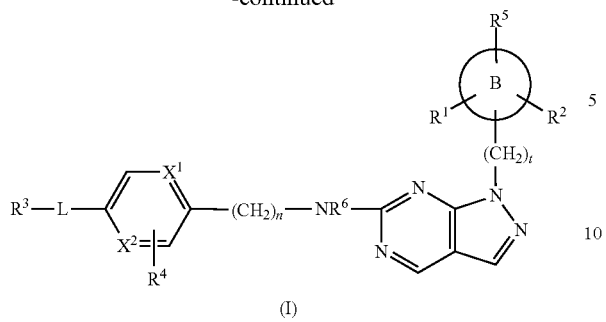

(I)

b) reacting an intermediate of formula (XIV) with an intermediate of formula (XVI-a) in the presence of a suitable solvent optionally in the presence of a suitable base with the formation of compounds of formula (I) wherein L is —(CH$_2$)$_r$—NH—C(═O)—, herein referred to as compounds of formula (I-a),

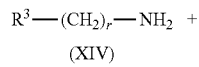

(XIV)

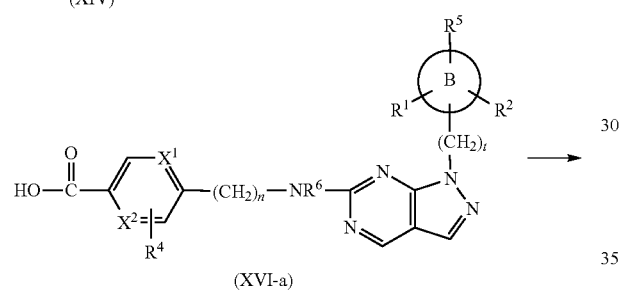

(XVI-a)

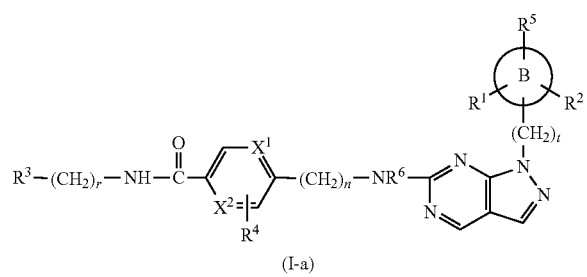

(I-a)

and c) reacting intermediates of formula (XIV) with intermediates of formula (XVI-b) in the presence of sodium triacetoxyborohydride or sodium cyanoborohydride, in the presence of a suitable acid and in a suitable solvent, resulting in compounds of formula (I) wherein L is —(CH$_2$)$_r$—NH—(CH$_2$)—, herein referred to as compounds of formula (I-b),

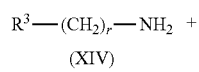

(XIV)

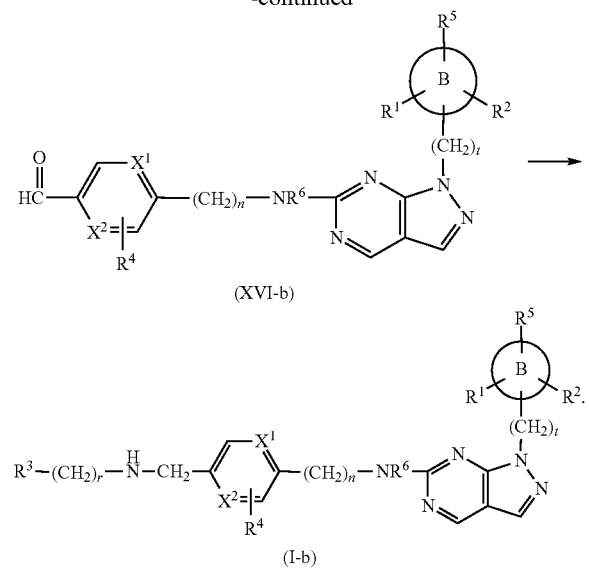

10. A compound as claimed in claim 2 wherein
X$^1$ and X$^2$ are each CH; n is 0; t is 0; ring B represents cyclohexyl, norbornyl or

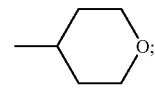

L is a direct bond, —(CH$_2$)$_r$—NR$^7$—(CH$_2$)$_s$—, —(CR$^8$$_2$)—O—(CH$_2$)$_s$—, —(CH$_2$)$_s$—O—C(═O)—, —(CH$_2$)$_r$—NR$^7$—C(═O)— or —(CH$_2$)$_r$—NH—S(═O)$_2$—; r is 0, 2 or 3; each R$^7$ is hydrogen or C$_{1-4}$alkyloxycarbonyl; each R$^8$ is independently hydrogen or hydroxy; R$^1$, R$^2$ and R$^5$ are each independently hydrogen; R$^3$ is C$_{1-6}$alkyloxy, —NR$^9$R$^{10}$, triazolyl, or

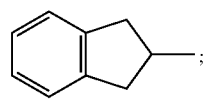

each R$^9$ and R$^{10}$ independently represent C$_{1-6}$alkyl; R$^4$ is hydrogen or R$^4$ together with -L-R$^3$— can form a bivalent radical of formula —NH—CH═CH—; and R$^6$ is hydrogen or C$_{1-4}$alkyloxycarbonyl.

11. A compound as claimed in claim 2 wherein X$^1$ and X$^2$ are each CH; n is 0; t is 0; ring B represents cyclohexyl or norbornyl; L is a direct bond, —(CH$_2$)$_r$—NR$^7$—(CH$_2$)$_s$—, —(CR$^8$$_2$)$_r$—O—(CH$_2$)$_s$— or —(CH$_2$)$_r$—NR$^7$—C(═O)—;
r is 0, 2 or 3; each R$^7$ is hydrogen; each R$^8$ is independently hydrogen or hydroxy;
R$^1$, R$^2$ and R$^5$ are each independently hydrogen; R$^3$ is C$_{1-6}$alkyloxy, —NR$^9$R$^{10}$, triazolyl, or

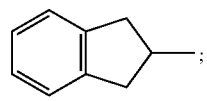

each $R^9$ and $R^{10}$ independently represent $C_{1-6}$alkyl; $R^4$ is hydrogen; and $R^6$ is hydrogen.

12. A compound as claimed in claim 3 wherein $X^1$ and $X^2$ are each CH; n is 0; t is 0; ring B represents cyclohexyl or norbornyl; L is a direct bond, —(CH$_2$)$_r$—NR$^7$—(CH$_2$)$_s$—, —(CR$^8{}_2$)$_r$—O—(CH$_2$)$_s$— or —(CH$_2$)$_r$—NR$^7$—C(=O);

r is 0, 2 or 3; each $R^7$ is hydrogen; each $R^8$ is independently hydrogen or hydroxy;

$R^1$, $R^2$ and $R^5$ are each independently hydrogen; $R^3$ is $C_{1-6}$alkyloxy, —NR$^9$R$^{10}$, triazolyl, or

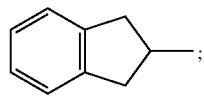;

each $R^9$ and $R^{10}$ independently represent $C_{1-6}$alkyl; $R^4$ is hydrogen; and $R^6$ is hydrogen.

13. A pharmaceutical composition comprising pharmaceutically acceptable carriers and as an active ingredient a therapeutically effective amount of a compound as claimed in claim 2.

14. A pharmaceutical composition comprising pharmaceutically acceptable carriers and as an active ingredient a therapeutically effective amount of a compound as claimed in claim 3.

15. A pharmaceutical composition comprising pharmaceutically acceptable carriers and as an active ingredient a therapeutically effective amount of a compound as claimed in claim 4.

16. A pharmaceutical composition comprising pharmaceutically acceptable carriers and as an active ingredient a therapeutically effective amount of a compound as claimed in claim 5.

* * * * *